United States Patent
Sasamoto

(10) Patent No.: US 8,988,516 B2
(45) Date of Patent: Mar. 24, 2015

(54) IMAGING DEVICE AND ENDOSCOPE

(71) Applicant: Olympus Medical Systems Corp., Tokyo (JP)

(72) Inventor: Tsutomu Sasamoto, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/100,630

(22) Filed: Dec. 9, 2013

(65) Prior Publication Data

US 2014/0092225 A1    Apr. 3, 2014

Related U.S. Application Data

(63) Continuation of application No. PCT/JP2012/069361, filed on Jul. 30, 2012.

(51) Int. Cl.
| | | |
|---|---|---|
| G02B 23/24 | (2006.01) | |
| H04N 5/225 | (2006.01) | |
| G03B 17/00 | (2006.01) | |
| G03B 9/02 | (2006.01) | |
| G02B 5/00 | (2006.01) | |
| A61B 1/00 | (2006.01) | |

(52) U.S. Cl.
CPC ............ *H04N 5/2254* (2013.01); *G03B 17/00* (2013.01); *G03B 9/02* (2013.01); *G02B 5/005* (2013.01); *G02B 23/243* (2013.01); *A61B 1/00163* (2013.01)
USPC ......................................................... 348/65

(58) Field of Classification Search
CPC .................................................. G02B 23/243
USPC ............................................................ 348/65
See application file for complete search history.

(56) References Cited

U.S. PATENT DOCUMENTS

| | | | | |
|---|---|---|---|---|
| 5,547,457 | A * | 8/1996 | Tsuyuki et al. | 600/175 |
| 6,069,651 | A * | 5/2000 | Tsuyuki et al. | 348/75 |
| 6,847,480 | B2 * | 1/2005 | Steenblik et al. | 359/368 |
| 7,160,249 | B2 * | 1/2007 | Hasegawa | 600/167 |

(Continued)

FOREIGN PATENT DOCUMENTS

| | | |
|---|---|---|
| JP | 54-020725 | 2/1979 |
| JP | 04-171415 | 6/1992 |

(Continued)

OTHER PUBLICATIONS

International Search Report, mailed Oct. 30, 2012, issued in corresponding International Application No. PCT/JP2012/069361.

*Primary Examiner* — William C Vaughn, Jr.
*Assistant Examiner* — Luis M Perez
(74) *Attorney, Agent, or Firm* — Kenyon & Kenyon LLP

(57) ABSTRACT

The depth of field is extended by using a simple structure. Provided is an imaging device comprising: an objective optical system that comprises an aperture stop that is disposed at an intermediate position on an optical axis and that has an opening that allows incident light from an object to pass therethrough; and an imaging element that acquires an optical image of the object, which is formed by the objective optical system, wherein pixels of the imaging element are arranged in a square along two mutually orthogonal axial directions, and the aperture stop includes a light-blocking portion at a portion aligned with the optical axis, the light-blocking portion having a square shape with sides inclined at 45° relative to the directions in which the pixels are arranged.

6 Claims, 32 Drawing Sheets

(56) References Cited

U.S. PATENT DOCUMENTS

| | | |
|---|---|---|
| 7,704,206 B2 * | 4/2010 | Suzuki et al. .................. 600/178 |
| 8,249,443 B2 * | 8/2012 | Ito et al. ........................ 396/275 |

FOREIGN PATENT DOCUMENTS

| | | |
|---|---|---|
| JP | 04-179958 | 6/1992 |
| JP | 04-251239 | 9/1992 |
| JP | 07-084221 | 3/1995 |
| JP | 09-243945 | 9/1997 |
| JP | 2000-098302 | 4/2000 |
| JP | 2003-235794 | 8/2003 |
| JP | 2004-341521 | 12/2004 |
| JP | 2004-537749 | 12/2004 |
| JP | 2007-227896 | 9/2007 |
| JP | 2008-511859 | 4/2008 |
| JP | 2009-288682 | 12/2009 |
| WO | 03/012528 | 2/2003 |
| WO | 2006/028527 | 3/2006 |

* cited by examiner

IMAGING DEVICE AND ENDOSCOPE

CROSS-REFERENCE TO RELATED APPLICATIONS

This is a continuation of International Application PCT/JP2012/069361, with an international filing date of Jul. 30, 2012, which is hereby incorporated by reference herein in its entirety. This application claims the benefit of Japanese Patent Application No. 2011-205912, the content of which is incorporated herein by reference.

TECHNICAL FIELD

The present invention relates to imaging devices and endoscopes.

BACKGROUND ART

In the related art, in optical systems provided in imaging devices such as endoscopes, a pupil modulation element is used as a means for extending the depth of field (for example, see Patent Literatures 1 and 2). A pupil modulation element has the effect of making the optical transfer function substantially constant over a wide depth of field.

CITATION LIST

Patent Literature

{PTL 1}
  Japanese Unexamined Patent Application, Publication No. 2000-98302
{PTL 2}
  Japanese Unexamined Patent Application, Publication No. 2003-235794

SUMMARY OF INVENTION

A first aspect of the present invention is an imaging device comprising: an objective optical system that comprises an aperture stop that is disposed at an intermediate position on an optical axis and that has an opening that allows incident light from an object to pass therethrough; and an imaging element that acquires an optical image of the object, which is formed by the objective optical system, wherein pixels of the imaging element are arranged in a square along two mutually orthogonal axial directions, and the aperture stop includes a light-blocking portion at a portion aligned with the optical axis, the light-blocking portion having a square shape with sides inclined at 45° relative to the directions in which the pixels are arranged.

A second aspect of the present invention is an endoscope including the imaging device as described above.

DESCRIPTION OF EMBODIMENT

An objective optical system 1 according to an embodiment of the present invention, as well as an imaging device 10 provided with the objective optical system 1, will be described below with reference to FIGS. 1 to 5.

Figure 1:
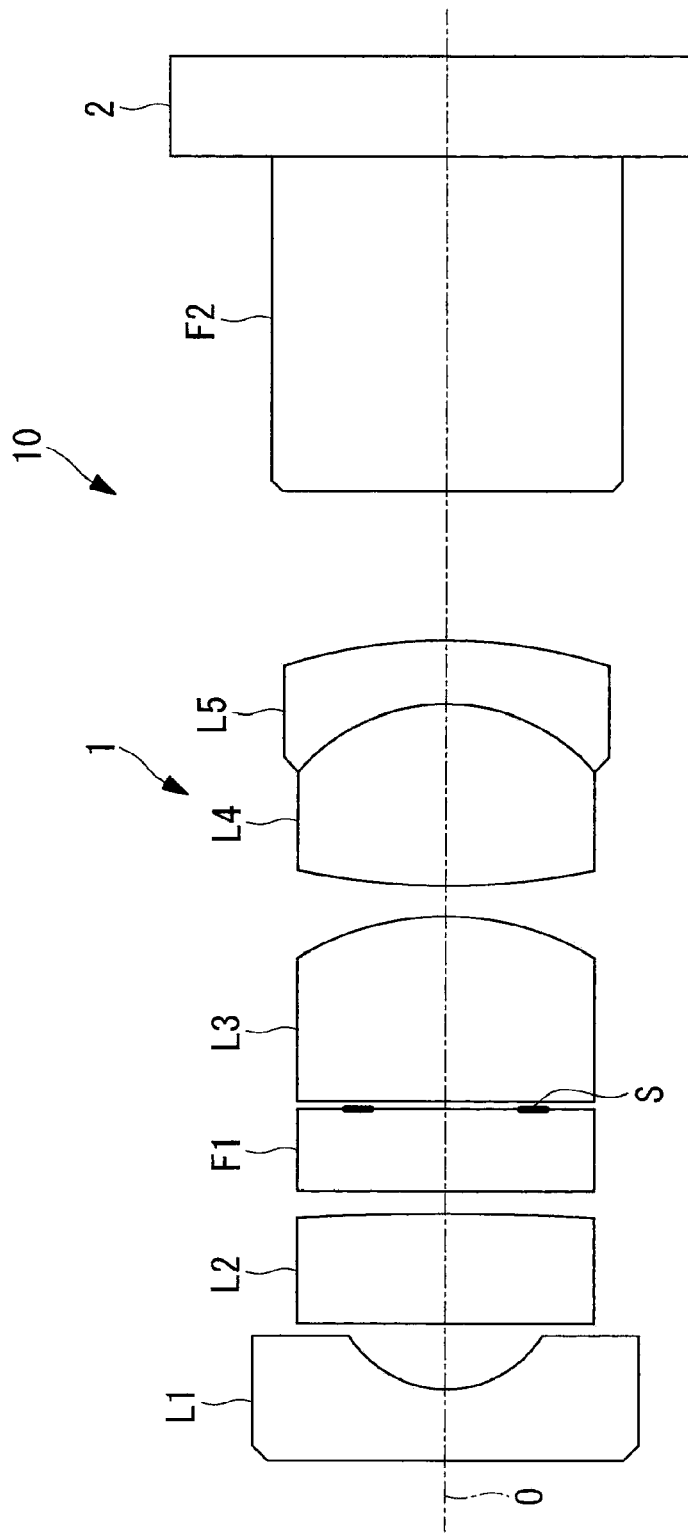
FIG. 1 is a lens cross-sectional diagram showing the overall structure of an objective optical system according to an embodiment of the present invention.

As shown in FIG. 1, the objective optical system 1 according to this embodiment includes, in order from the object side, first to fifth lenses L1 to L5, parallel flat plates F1 and F2 disposed between the second lens and the third lens and on the image side of the fifth lens, and an aperture stop S formed on the image-side surface of the parallel flat plate F1.

The first to fifth lenses L1 to L5 are formed from single glass materials and have optical characteristics that are rotationally symmetric about the optical axis O.

Figure 2:
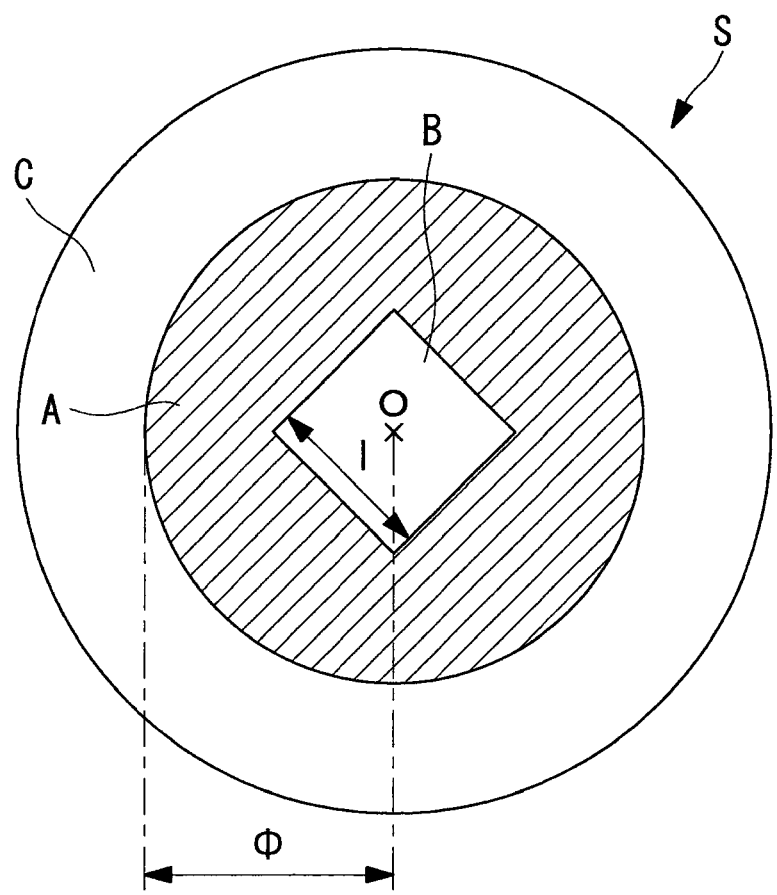
FIG. 2 is a front view of an aperture stop provided in the objective optical system in FIG. 1.

The parallel flat plates F1 and F2 are cover glasses or the like made from optically transparent glass materials. As shown in FIG. 2, the aperture stop S includes an opening (the region shown with hatching) A that allows incident light that is incident on the first lens L1 from the object (not illustrated) to pass therethrough and a light-blocking portion B formed at a position aligned with the optical axis O of the objective optical system 1 for blocking the incident light. The opening A has a circular outer shape of radius Φ, centered on the optical axis O. The light-blocking portion B has a square shape with a side length of l centered on the optical axis O and has a point-symmetrical shape with respect to the optical axis.

The aperture stop S is fabricated by forming a peripheral portion C of the opening A and the light-blocking portion B by forming a metal film directly on the image-side surface of the parallel flat plate F1 by vapor deposition or the like. By doing so, it is possible to easily fabricate the aperture stop S having a structure in which the light-blocking portion B is provided at the center of the opening A.

Note that the aperture stop S may be fabricated by forming a metal film on a flat surface, such as that of a plano-convex lens or the like. In addition, although a peripheral portion C whose outer form is circular is illustrated in FIG. 2 as an example, the outer form of the peripheral portion C is not particularly restricted and may be, for example, rectangular or the like.

The aperture stop S satisfies conditional expression (1) below:

$$4 < Q < 50 \qquad (1)$$

where $Q = $ (area of light-blocking portion B/area of opening A)$\times 100$.

Conditional expression (1) defines the ratio of the area of the opening A to the area of the light-blocking portion B. By satisfying the conditional expression (1), a sufficient intensity of incident light passing through the opening A can be ensured, and thus, the advantageous effect of extending the depth of field by using the light-blocking portion B can be sufficiently obtained. A Q value of 4 or less is undesirable because an adequate depth-of-field extending effect (described later) cannot be achieved by the aperture stop S. On the other hand, a Q value of 50 or higher is undesirable because the quality of the image obtained by the imaging element 2 is degraded due to excessive blocking of the incident light.

The aperture stop S preferably satisfies conditional expression (1-1) below, more preferably satisfies conditional expression (1-2), and most preferably satisfies conditional expression (1-3).

$$15 < Q < 40 \qquad (1\text{-}1)$$

$$15 < Q < 35 \qquad (1\text{-}2)$$

$$20 < Q < 35 \qquad (1\text{-}3)$$

The objective optical system 1 according to this embodiment constitutes the imaging device 10 together with an imaging element 2, such as a CCD or CMOS device. The imaging device 10, in which the parallel flat plate F2 is connected to a glass lid that covers the imaging surface of the imaging element 2, acquires an optical image of an object formed on the imaging surface.

Figure 3A:
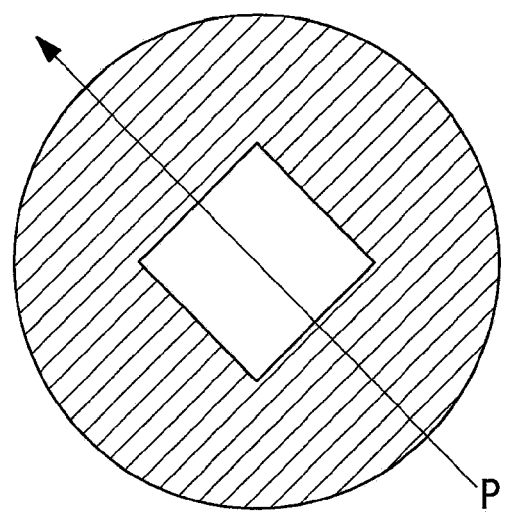
FIG. 3A is a diagram for explaining the positional relationship of the aperture stop in FIG. 2 and the directions in which pixels of an imaging element are arranged, showing the aperture stop in FIG. 2.
Figure 3B:
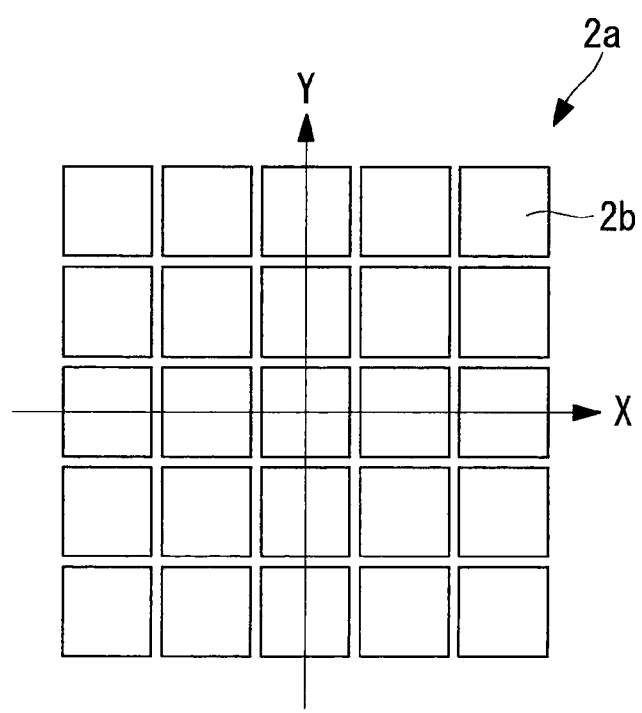
FIG. 3B is a diagram for explaining the positional relationship of the aperture stop in FIG. 2 and the directions in which the pixels of the imaging element are arranged, showing the arrangement of the pixels of the imaging element.

As shown in FIG. 3B, in the imaging surface 2a, pixels 2b are arranged in a square along two mutually orthogonal axial directions (the X-axis direction and the Y-axis direction). As shown in FIG. 3A, the objective optical system 1 is arranged relative to the imaging element 2 so that the edge direction (see arrow P) of the light-blocking portion B of the aperture stop S is inclined at 45° relative to the X-axis direction and the Y-axis direction, which are the directions in which the pixels are arranged. In this way, the light-blocking portion B has a shape formed by joining points that are inversely proportional to the distance from the center of one pixel to a pixel adjacent to that pixel, whereby an advantageous effect of extending the depth of field due to the light-blocking portion B, described later, is exhibited equally in each direction of the image, which is desirable.

Next, the operation of the thus-configured objective optical system 1 and the imaging device 10 provided therewith will be described.

Figure 4:
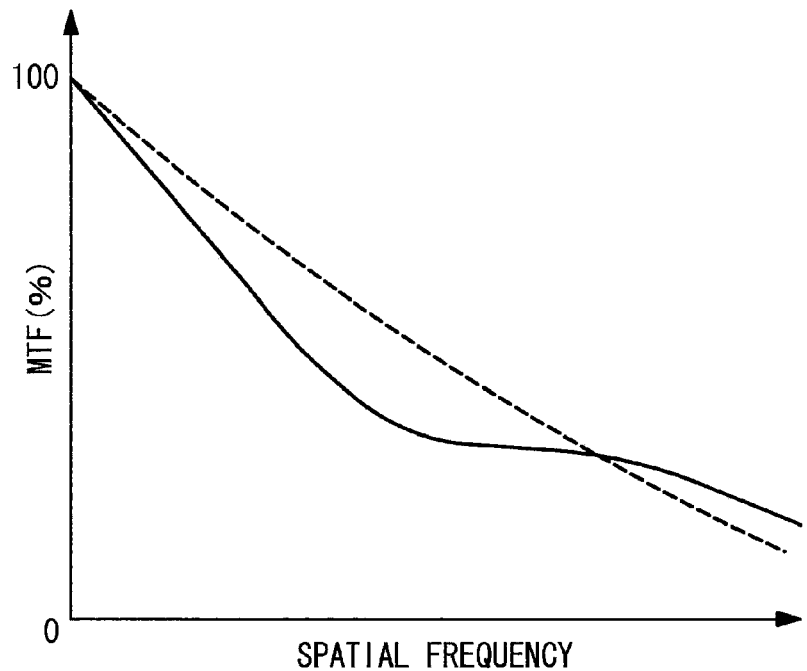
FIG. 4 is a graph showing an example MTF of the objective optical system in FIG. 1 and an example MTF of a conventional objective optical system.

The MTF of the objective optical system 1 according to this embodiment has characteristics such as those shown by the solid line in FIG. 4. That is to say, in the low-frequency region, the MTF (vertical axis) monotonically decreases as the spatial frequency (horizontal axis) increases, whereas in the high-frequency region, the MTF temporarily stops decreasing and becomes substantially horizontal. Here, the MTF is a function showing the contrast response with respect to the spatial frequency of the image, and as the MTF at a certain spatial frequency increases, a structure with dimensions corresponding to that spatial frequency can be resolved more clearly. Therefore, with the objective optical system 1 having the MTF characteristics shown in FIG. 4, a sufficiently high resolution is maintained even in the high-frequency region.

Such MTF characteristics are explained as follows. The MTF is represented by the autocorrelation function of the pupil function. The autocorrelation function of the pupil function of the objective optical system 1 according to this embodiment temporarily stops decreasing due to the existence of the light-blocking portion B at the position of the optical axis, corresponding to the center position of the pupil. Accordingly, the MTF also stops decreasing in the high-frequency region.

As a reference example of this embodiment, the MTF of an objective optical system provided with a conventional aperture stop formed only of an opening, without a light-blocking portion, is shown by the broken line in FIG. 4. With such a conventional objective optical system, the MTF continuously decreases in a monotonic fashion from the low-frequency side to the high-frequency side.

With the objective optical system 1 and the imaging device 10 according to this embodiment, the range in which the MTF has a sufficiently high value in the high-frequency region, for example, the range in which the MTF exceeds 10%, is extended. This means that the range in the direction of the optical axis O of the field of view where sufficiently high resolution is achieved is extended; in other words, the depth of field is effectively extended. Thus, this embodiment offers an advantage in that it is possible to effectively extend the depth of field while maintaining a simple structure in which the light-blocking portion B is merely provided at a position aligned with the optical axis O of the aperture stop S.

In addition, since all of the lenses L1 to L5 and the aperture stop S constituting the objective optical system 1 have optical characteristics that are rotationally symmetric with respect to the optical axis O, the optical image formed on the imaging surface 2c does not contain any aberration components that are asymmetric with respect to the optical axis O. Thus, an advantage is afforded in that it is possible to exhibit the advantageous effect of image processing to the fullest extent. Also, with an endoscope provided with the imaging device 10 according to this embodiment, an advantage is afforded in that it is possible to obtain a clear image over a sufficiently wide depth of field, without relying on a special image processing apparatus, zoom function, or the like.

The MTF of the objective optical system 1 according to this embodiment shows a tendency to decrease in the low-frequency region compared with the objective optical system using the conventional aperture stop. Such a drop in resolution in the low-frequency region is sufficiently well-corrected by subjecting the image obtained by the imaging element 2 to image processing. The image processing is designed so that, for example, the low-frequency region of the MTF has prescribed characteristics on the bases of the results calculated by the simulation of MTF of the objective optical system 1.

In this embodiment, although a square light-blocking portion B is illustrated as an example, the shape of the light-blocking portion B is not restricted thereto. For example, in FIG. 2, the light-blocking portion B may be circular. Also, a plurality of openings may be provided around the optical axis O. With this arrangement too, the MTF in the high-frequency region can be improved while maintaining a simple, low-cost structure, and the depth of field can be extended. In addition, the shape of the peripheral portion C of the opening A is also not restricted to a circular shape like that shown in FIG. 2, and other shapes may be used.

Figure 5:
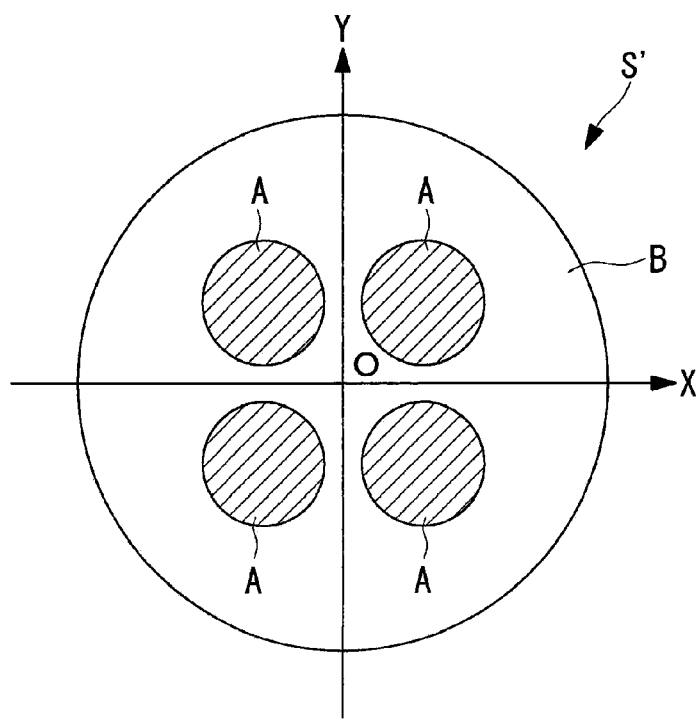
FIG. 5 is a front view of a modification of the aperture stop in FIG. 2.

As shown in FIG. 5, in the case where a plurality of openings A are provided, the openings A are preferably arranged regularly with respect to the optical axis O along the directions in which the pixels are arranged (X-axis direction and Y-axis direction). With such an arrangement, it is possible to extend the depth of field equally at each position in the image.

An aperture stop S' shown in FIG. 5 is easily fabricated by forming the light-blocking portion B by forming a metal film on a lens surface, similarly to the aperture stop S shown in FIG. 2. Also, the aperture stop S' can be easily fabricated by processing through-holes in a flat plate formed of a material having light-blocking properties, such as a metal etc., to form the openings A.

Examples

Next, Examples 1 to 14 of the above embodiment will be described with reference to FIGS. 6 to 34. The structure of the objective optical system in each Example will be described first, and the advantageous effect of extending the depth of field achieved by each objective optical system will be described after the description of the structure. In the lens data given in each Example, r is the radius of curvature, d is the inter-surface spacing, ne is the refractive index at the e-line, vd is the Abbe number at the d-line, OBJ is the object plane, and IMG is the image plane. Also, the surface number corresponding to the aperture stop has S appended thereto. In the lens cross-sectional diagrams, IMG indicates the image plane.

Example 1

Figure 6:
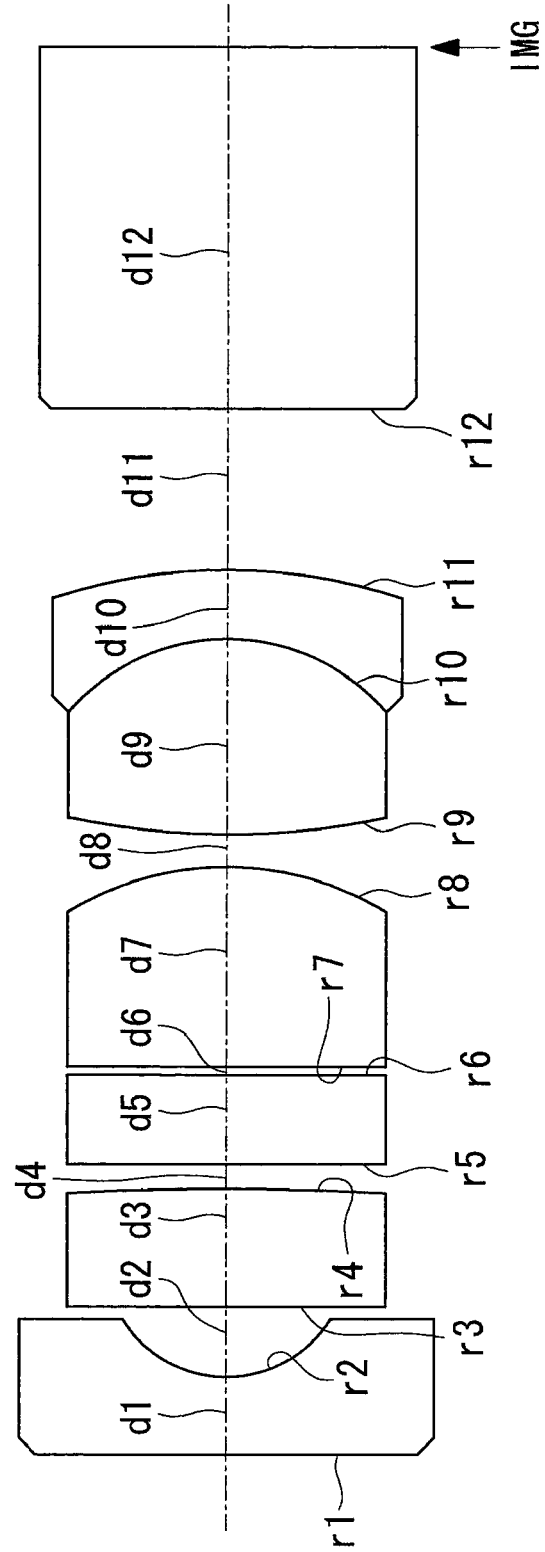
FIG. 6 is a lens cross-sectional diagram showing the overall structure of an objective optical system according to Example 1 of the present invention.
Figure 7:
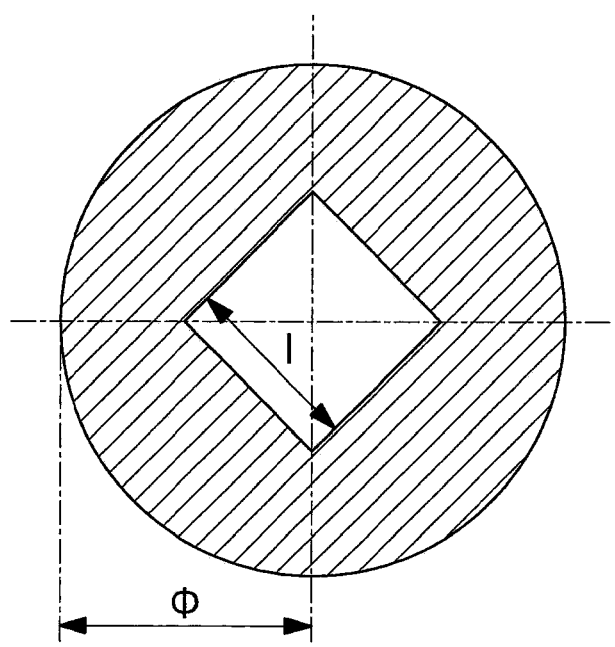
FIG. 7 is a front view of an aperture stop provided in the objective optical system of Example 1 of the present invention.

An objective optical system according to Example 1 of the present invention has a lens structure shown in FIG. 6 and the following lens data. The aperture stop in this Example is formed on the image-side surface of a cover glass (Surface No. 6). As shown in FIG. 7, the aperture stop includes an opening having a circular outer shape with a radius $\Phi=0.33$ mm centered on the optical axis and a light-blocking portion with a square shape of side length l=0.226 mm centered on the optical axis. In conditional expression (1), Q=14.9.

| lens data | | | | |
|---|---|---|---|---|
| surface number | r | d | ne | vd |
| OBJ | ∞ | 17.00 | 1. | |
| 1 | ∞ | 0.47 | 1.88815 | 40.76 |
| 2 | 0.8120 | 0.42 | 1. | |
| 3 | ∞ | 0.73 | 1.93429 | 18.90 |
| 4 | 20.4054 | 0.15 | 1. | |
| 5 | ∞ | 0.56 | 1.51564 | 75.00 |
| 6(S) | ∞ | 0.05 | 1. | |
| 7 | ∞ | 1.23 | 1.88815 | 40.76 |
| 8 | −1.9073 | 0.20 | 1. | |
| 9 | 5.9797 | 1.18 | 1.73234 | 54.68 |
| 10 | −1.3347 | 0.43 | 1.93429 | 18.90 |
| 11 | −3.8757 | 0.97 | 1. | |
| 12 | ∞ | 2.20 | 1.51825 | 64.14 |
| IMG | ∞ | 0.00 | | |
| Miscellaneous Data | | | | |
| Image height | | | 0.986 | |
| Focal distance | | | 1.000 | |
| Total lens length | | | 8.582 | |

Example 2

Figure 8:
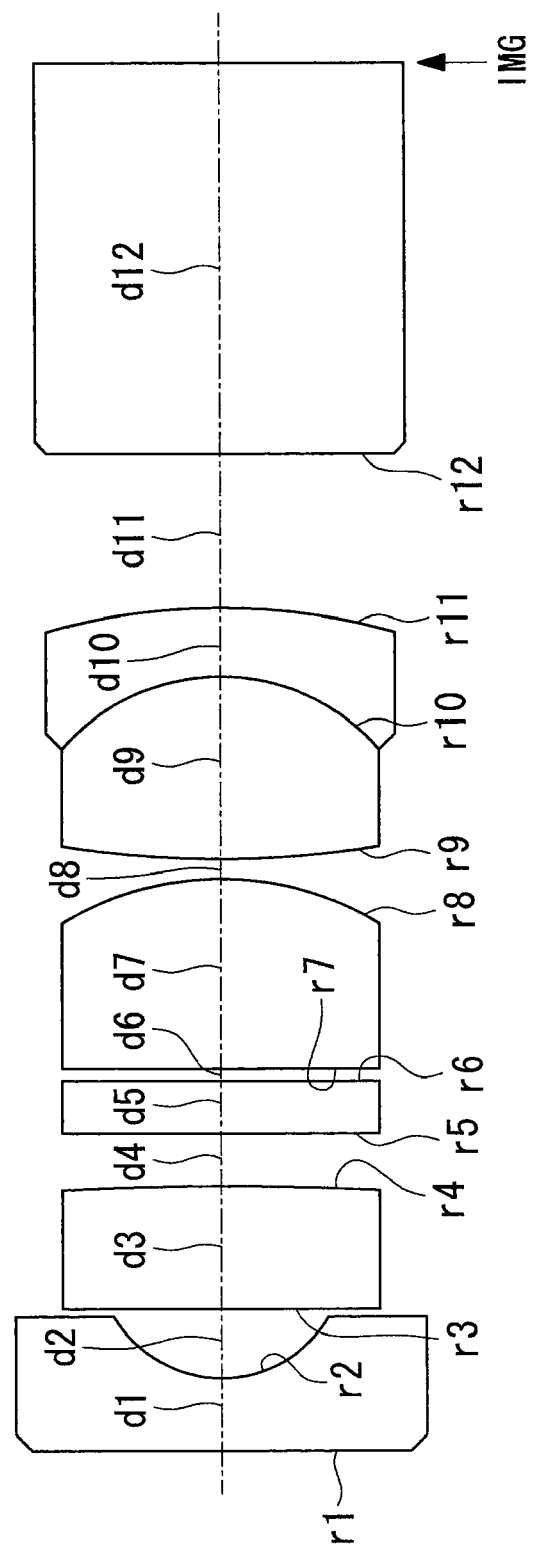
FIG. 8 is a lens cross-sectional diagram showing the overall structure of an objective optical system according to Example 2 of the present invention.
Figure 9:
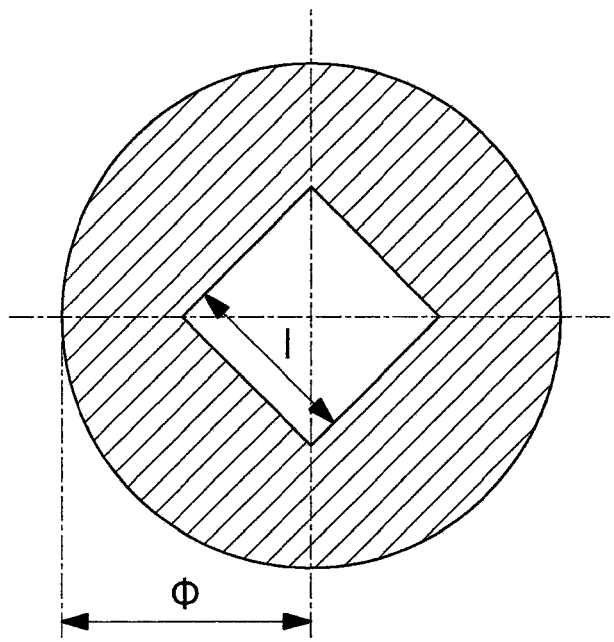
FIG. 9 is a front view of an aperture stop provided in the objective optical system of Example 2 of the present invention.

An objective optical system according to Example 2 of the present invention has a lens structure shown in FIG. 8 and the following lens data. The aperture stop in this Example is formed on the image-side surface of a cover glass (Surface No. 6). As shown in FIG. 9, the aperture stop includes an opening having a circular outer shape with a radius Φ=0.32 mm centered on the optical axis and a light-blocking portion with a square shape of side length l=0.226 mm centered on the optical axis. In conditional expression (1), Q=15.9.

| | | lens data | | |
|---|---|---|---|---|
| surface number | r | d | ne | νd |
| OBJ | ∞ | 15.20 | 1. | |
| 1 | ∞ | 0.45 | 1.88815 | 40.76 |
| 2 | 0.8070 | 0.42 | 1. | |
| 3 | ∞ | 0.75 | 1.93429 | 18.90 |
| 4 | −18.8610 | 0.32 | 1. | |
| 5 | ∞ | 0.33 | 1.51564 | 75.00 |
| 6(S) | ∞ | 0.06 | 1. | |
| 7 | ∞ | 1.20 | 1.88815 | 40.76 |
| 8 | −1.9010 | 0.10 | 1. | |
| 9 | 6.3883 | 1.14 | 1.73234 | 54.68 |
| 10 | −1.3423 | 0.43 | 1.93429 | 18.90 |
| 11 | −3.9950 | 0.94 | 1. | |
| 12 | ∞ | 2.40 | 1.51825 | 64.14 |
| IMG | ∞ | 0.00 | | |

| Miscellaneous Data | |
|---|---|
| Image height | 0.943 |
| Focal distance | 1.00003 |
| Total lens length | 8.537 |
| F-number | 1.356 |
| Viewing angle | 128.8° |

Example 3

Figure 10:
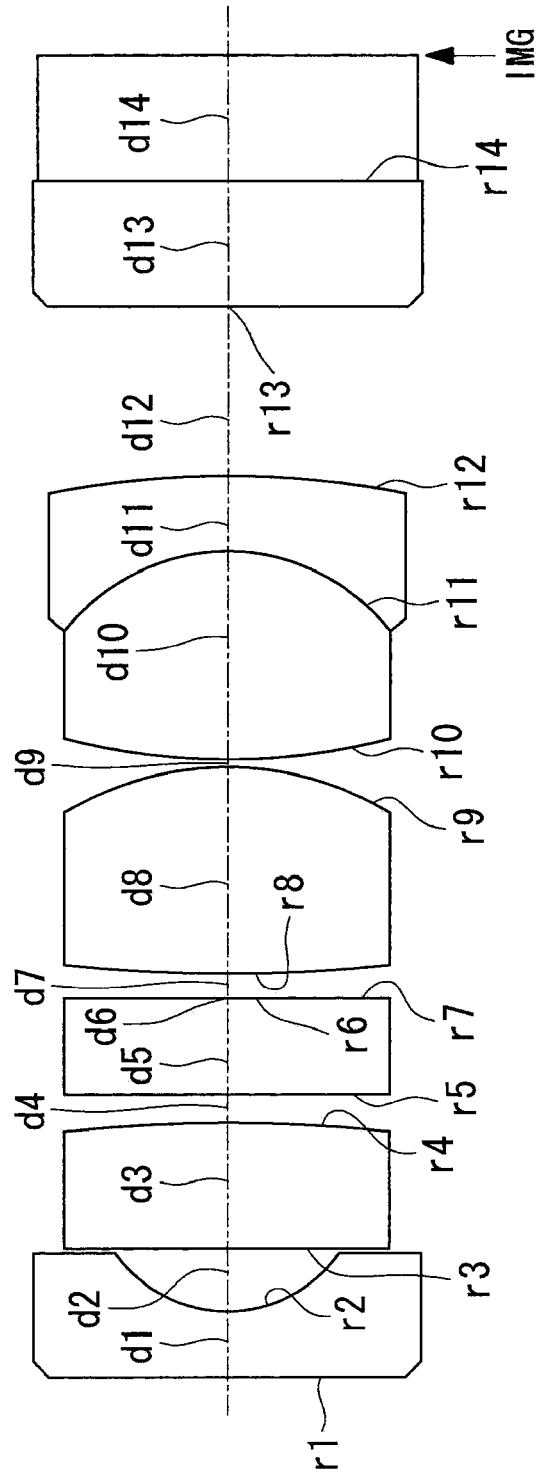
FIG. 10 is a lens cross-sectional diagram showing the overall structure of an objective optical system according to Example 3 of the present invention.
Figure 11:
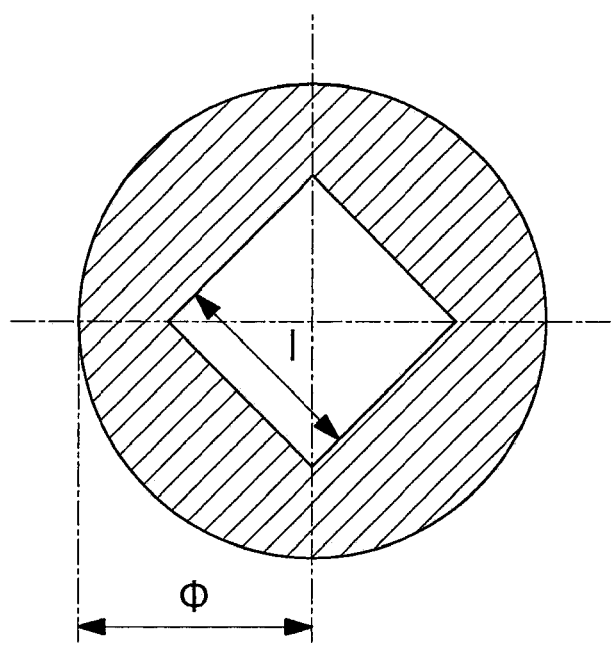
FIG. 11 is a front view of an aperture stop provided in the objective optical system of Example 3 of the present invention.

An objective optical system according to Example 3 of the present invention has a lens structure shown in FIG. 10 and the following lens data. The aperture stop in this Example is formed on an image-side surface of a cover glass (Surface No. 6). As shown in FIG. 11, the aperture stop includes an opening having a circular outer shape with a radius Φ=0.2465 mm centered on the optical axis and a light-blocking portion with a square shape of side length l=0.226 mm centered on the optical axis. In conditional expression (1), Q=26.8.

| | | lens data | | |
|---|---|---|---|---|
| surface number | r | d | ne | νd |
| OBJ | ∞ | 15.00 | 1. | |
| 1 | ∞ | 0.41 | 1.88815 | 40.76 |
| 2 | 0.8450 | 0.38 | 1. | |
| 3 | ∞ | 0.74 | 1.85504 | 23.78 |
| 4 | −9.6236 | 0.19 | 1. | |
| 5 | ∞ | 0.57 | 1.51564 | 75.00 |
| 6(S) | ∞ | 0.00 | 1. | |
| 7 | ∞ | 0.16 | 1. | |
| 8 | 9.4949 | 1.25 | 1.83932 | 37.16 |
| 9 | −1.9712 | 0.05 | 1. | |
| 10 | 3.9867 | 1.25 | 1.69979 | 55.53 |
| 11 | −1.2696 | 0.43 | 1.93429 | 18.90 |
| 12 | −5.8760 | 1.04 | 1. | |
| 13 | ∞ | 0.75 | 1.51825 | 64.14 |
| 14 | ∞ | 0.75 | 1.61379 | 50.20 |
| IMG | ∞ | 0.00 | | |

| Miscellaneous Data | |
|---|---|
| Image height | 0.96 |
| Focal distance | 1.00215 |
| Total lens length | 7.968 |
| F-number | 1.319 |
| Viewing angle | 130.8° |

Example 4

Figure 12:
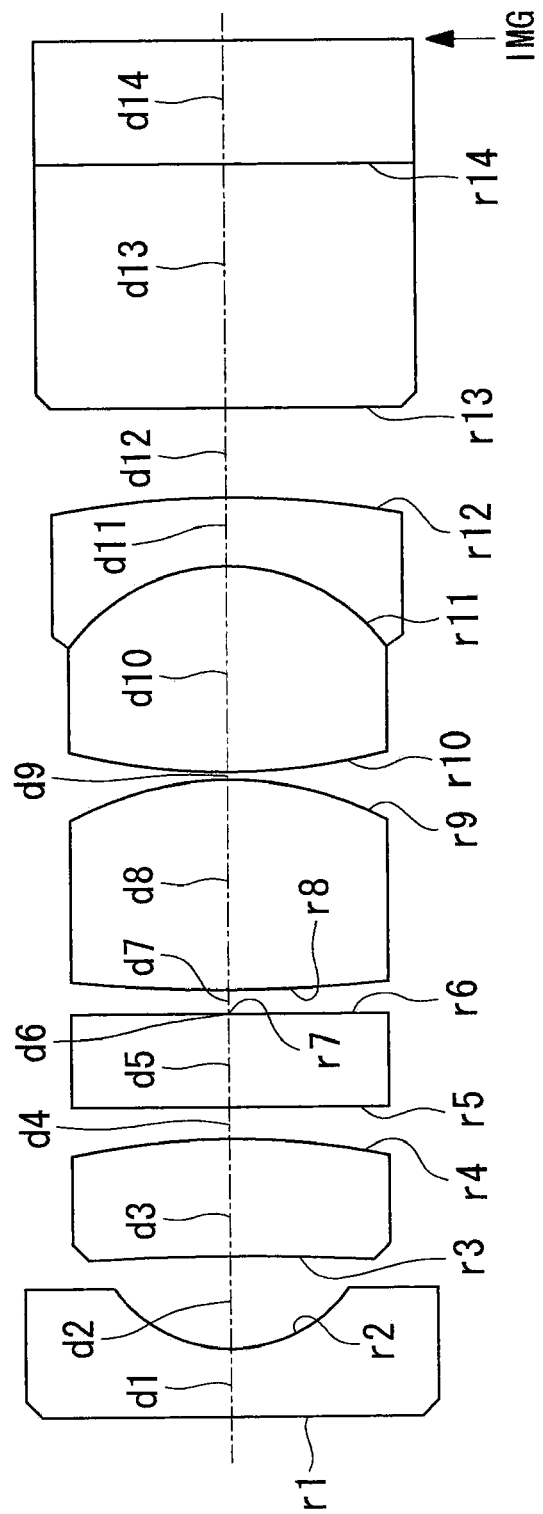
FIG. 12 is a lens cross-sectional diagram showing the overall structure of an objective optical system according to Example 4 of the present invention.
Figure 13:
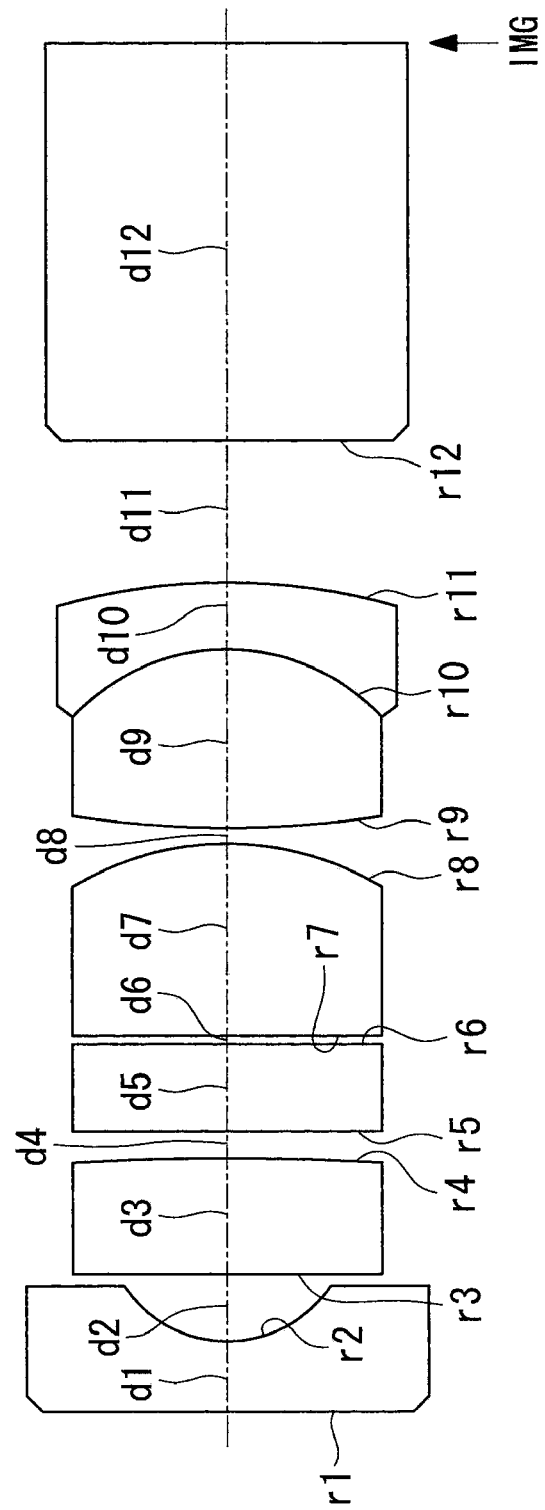
FIG. 13 is a front view of an aperture stop provided in the objective optical system of Example 4 of the present invention.

An objective optical system according to Example 4 of the present invention has a lens structure shown in FIG. 12 and the following lens data. The aperture stop in this Example is formed on the image-side surface of the cover glass (Surface No. 7). As shown in FIG. 13, the aperture stop includes an opening having a circular outer shape with a radius Φ=0.224 mm centered on the optical axis and a light-blocking portion with a square shape of side length l=0.226 mm centered on the optical axis. In conditional expression (1), Q=32.4.

| | | lens data | | |
|---|---|---|---|---|
| surface number | r | d | ne | νd |
| OBJ | ∞ | 12.50 | 1. | |
| 1 | ∞ | 0.41 | 1.88815 | 40.76 |
| 2 | 0.8765 | 0.59 | 1. | |
| 3 | −10.1322 | 0.73 | 1.85504 | 23.78 |
| 4 | −4.2878 | 0.18 | 1. | |
| 5 | ∞ | 0.57 | 1.51564 | 75.00 |
| 6 | ∞ | 0.00 | 1. | |
| 7(S) | ∞ | 0.16 | 1. | |
| 8 | 9.6120 | 1.30 | 1.83932 | 37.16 |
| 9 | −2.0932 | 0.05 | 1. | |
| 10 | 4.5979 | 1.27 | 1.69979 | 55.53 |
| 11 | −1.2298 | 0.44 | 1.93429 | 18.90 |
| 12 | −6.2165 | 0.54 | 1. | |
| 13 | ∞ | 1.50 | 1.51825 | 64.14 |
| 14 | ∞ | 0.75 | 1.61379 | 50.20 |
| IMG | ∞ | 0.00 | | |

| Miscellaneous Data | |
|---|---|
| Image height | 0.96 |
| Focal distance | 1. |
| Total lens length | 8.487 |
| F-number | 1.644 |
| Viewing angle | 129.9° |

Example 5

Figure 14:
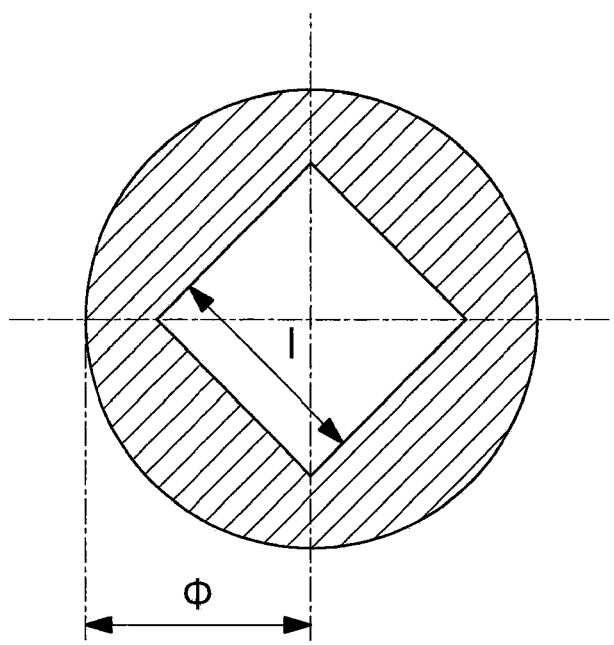
FIG. 14 is a lens cross-sectional diagram showing the overall structure of an objective optical system according to Example 5 of the present invention.
Figure 15:
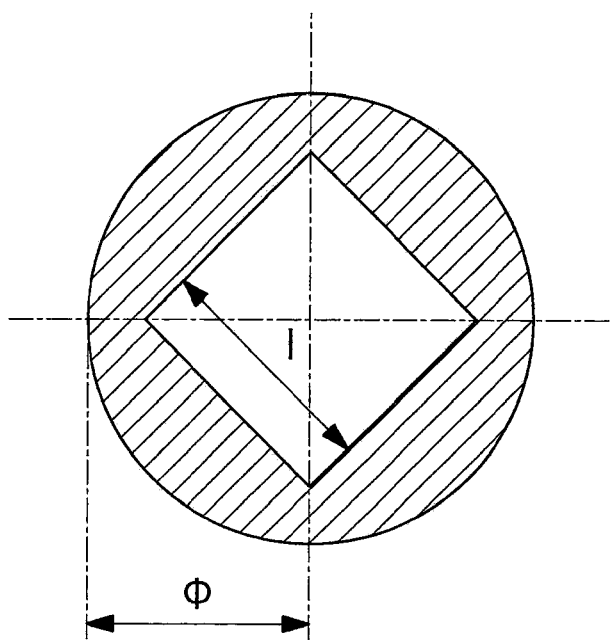
FIG. 15 is a front view of an aperture stop provided in the objective optical system of Example 5 of the present invention.

An objective optical system according to Example 5 of the present invention has a lens structure shown in FIG. 14 and the following lens data. The aperture stop in this Example is formed on the object-side surface of a cover glass (Surface No. 5). As shown in FIG. 15, the aperture stop includes an opening having a circular outer shape with a radius Φ=0.225 mm centered on the optical axis and a light-blocking portion with a square shape of side length l=0.24 mm centered on the optical axis. In conditional expression (1), Q=36.2.

| lens data | | | | |
|---|---|---|---|---|
| surface number | r | d | ne | vd |
| OBJ | ∞ | 11.50 | 1. | |
| 1 | ∞ | 0.45 | 1.88815 | 40.76 |
| 2 | 0.8064 | 0.42 | 1. | |
| 3 | ∞ | 0.73 | 1.85504 | 23.78 |
| 4 | −16.2332 | 0.17 | 1. | |
| 5 | ∞ | 0.56 | 1.51564 | 75.00 |
| 6(S) | ∞ | 0.03 | 1. | |
| 7 | ∞ | 1.24 | 1.88815 | 40.76 |
| 8 | −1.8966 | 0.09 | 1. | |
| 9 | 6.4116 | 1.13 | 1.73234 | 54.68 |
| 10 | −1.3374 | 0.43 | 1.93429 | 18.90 |
| 11 | −4.0282 | 0.89 | 1. | |
| 12 | ∞ | 2.50 | 1.51825 | 64.14 |
| IMG | ∞ | 0.00 | | |

| Miscellaneous Data | |
|---|---|
| Image height | 0.943 |
| Focal distance | 1.000 |
| Total lens length | 8.649 |
| F-number | 1.703 |
| Viewing angle | 127.6° |

Example 6

Figure 16:
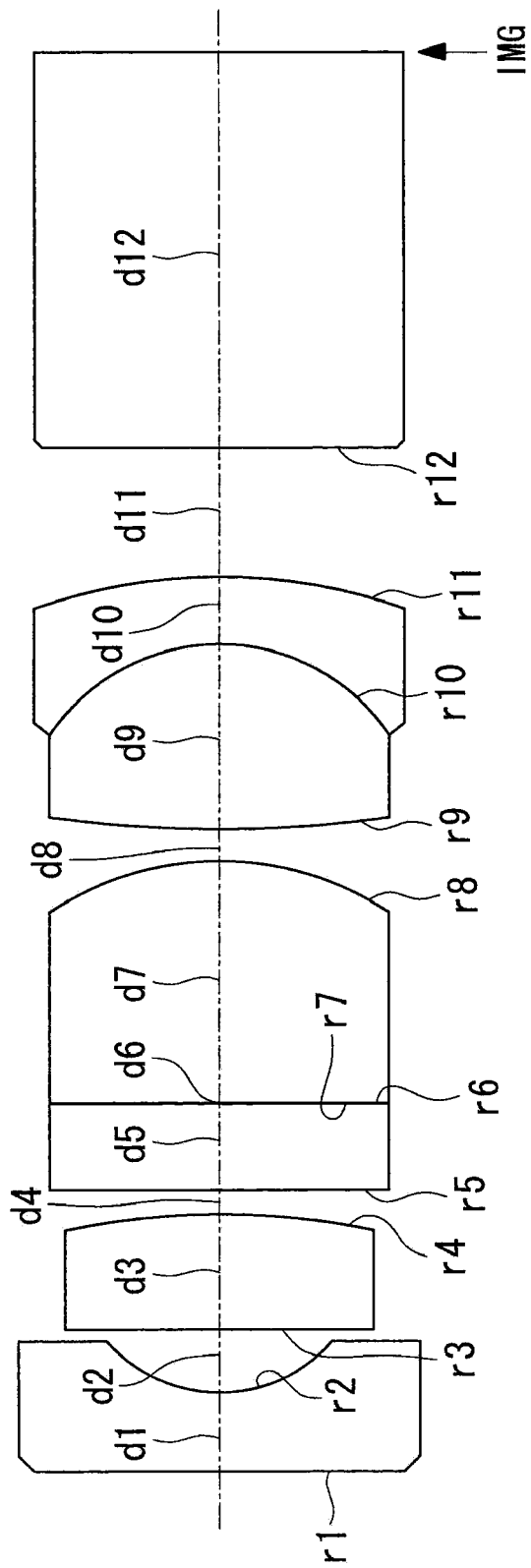
FIG. 16 is a lens cross-sectional diagram showing the overall structure of an objective optical system according to Example 6 of the present invention.
Figure 17:
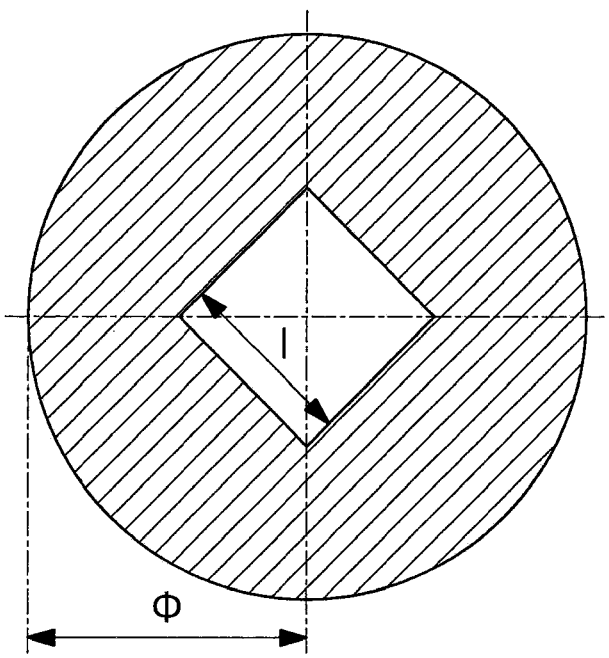
FIG. 17 is a front view of an aperture stop provided in the objective optical system of Example 6 of the present invention.

An objective optical system according to Example 6 of the present invention has a lens structure shown in FIG. 16 and the following lens data. The aperture stop in this Example is formed on the joining surface of a cover glass and a plano-convex lens (Surface No. 6). As shown in FIG. 17, the aperture stop includes an opening having a circular outer shape with a radius Φ=0.28 mm centered on the optical axis and a light-blocking portion with a square shape of side length l=0.184 mm centered on the optical axis. In conditional expression (1), Q=13.7.

| lens data | | | | |
|---|---|---|---|---|
| surface number | r | d | ne | vd |
| OBJ | ∞ | 19.50 | 1. | |
| 1 | ∞ | 0.50 | 2.18246 | 33.01 |
| 2 | 0.9683 | 0.42 | 1. | |
| 3 | ∞ | 0.72 | 1.93429 | 18.90 |
| 4 | −5.4027 | 0.15 | 1. | |
| 5 | ∞ | 0.56 | 1.51564 | 75.00 |
| 6(S) | ∞ | 0.00 | 1. | |
| 7 | ∞ | 1.54 | 1.88815 | 40.76 |
| 8 | −2.0953 | 0.20 | 1. | |
| 9 | 6.8599 | 1.18 | 1.73234 | 54.68 |
| 10 | −1.3201 | 0.43 | 1.93429 | 18.90 |
| 11 | −3.7233 | 0.83 | 1. | |
| 12 | ∞ | 2.50 | 1.51825 | 64.14 |
| IMG | ∞ | 0.00 | | |

| Miscellaneous Data | |
|---|---|
| Image height | 0.94 |
| Focal distance | 0.99999 |
| Total lens length | 9.024 |
| F-number | 1.56 |
| Viewing angle | 127.7° |

Example 7

Figure 18:
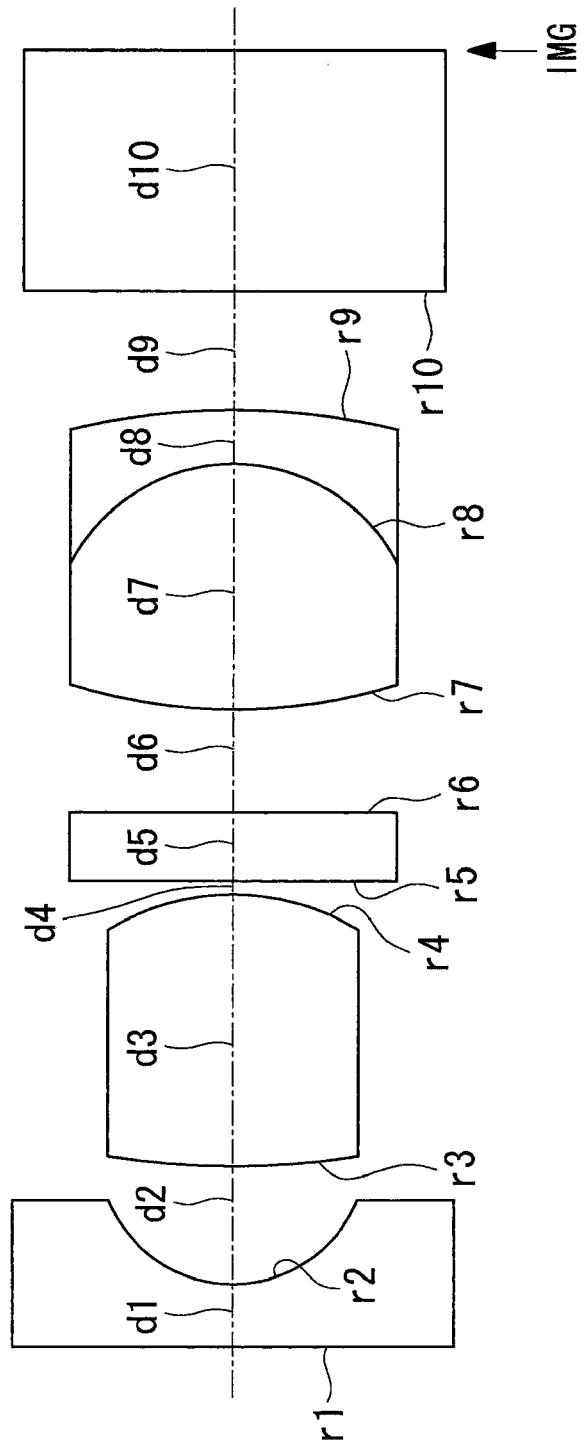
FIG. 18 is a lens cross-sectional diagram showing the overall structure of an objective optical system according to Example 7 of the present invention.
Figure 19:
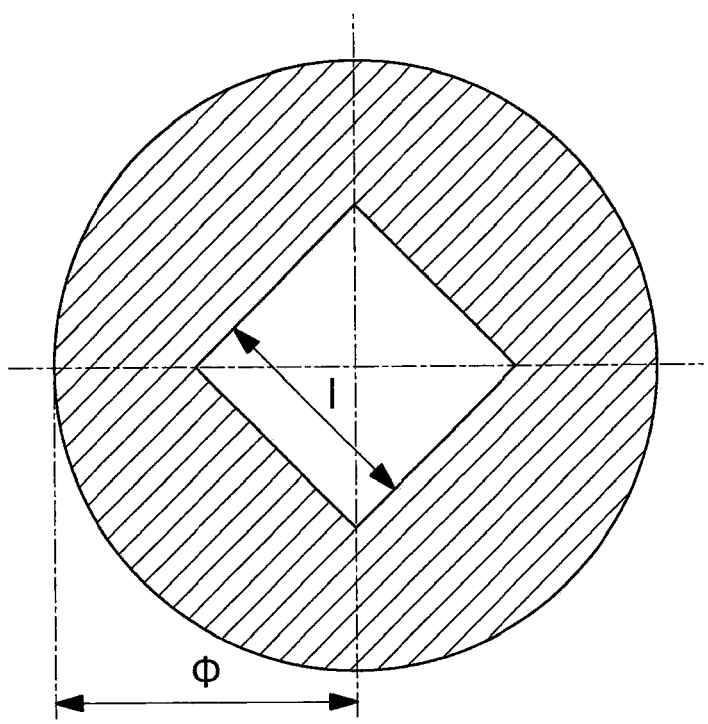
FIG. 19 is a front view of an aperture stop provided in the objective optical system of Example 7 of the present invention.

An objective optical system according to Example 7 of the present invention has a lens structure shown in FIG. 18 and the following lens data. The aperture stop in this Example is formed on the object-side surface of a cover glass (Surface No. 5). As shown in FIG. 19, the aperture stop includes an opening having a circular outer shape with a radius Φ=0.27 mm centered on the optical axis and a light-blocking portion with a square shape of side length l=0.198 mm centered on the optical axis. In conditional expression (1), Q=17.1.

| lens data | | | | |
|---|---|---|---|---|
| surface number | r | d | ne | vd |
| OBJ | ∞ | 18.10 | 1. | |
| 1 | ∞ | 0.33 | 1.88814 | 40.78 |
| 2 | 0.6783 | 0.60 | 1. | |
| 3 | 3.5348 | 1.37 | 1.73234 | 54.68 |
| 4 | −1.3630 | 0.09 | 1. | |
| 5(S) | ∞ | 0.35 | 1.52495 | 59.89 |
| 6 | ∞ | 0.52 | 1. | |
| 7 | 2.9104 | 1.26 | 1.69979 | 55.53 |
| 8 | −0.9191 | 0.26 | 1.85504 | 23.78 |
| 9 | −3.8252 | 0.61 | 1. | |
| 10 | ∞ | 1.23 | 1.51825 | 64.14 |
| IMG | ∞ | 0.00 | | |

| Miscellaneous Data | |
|---|---|
| Image height | 0.895 |
| Focal distance | 0.99988 |
| Total lens length | 6.608 |
| F-number | 4.236 |
| Viewing angle | 117.1° |

Example 8

Figure 20:
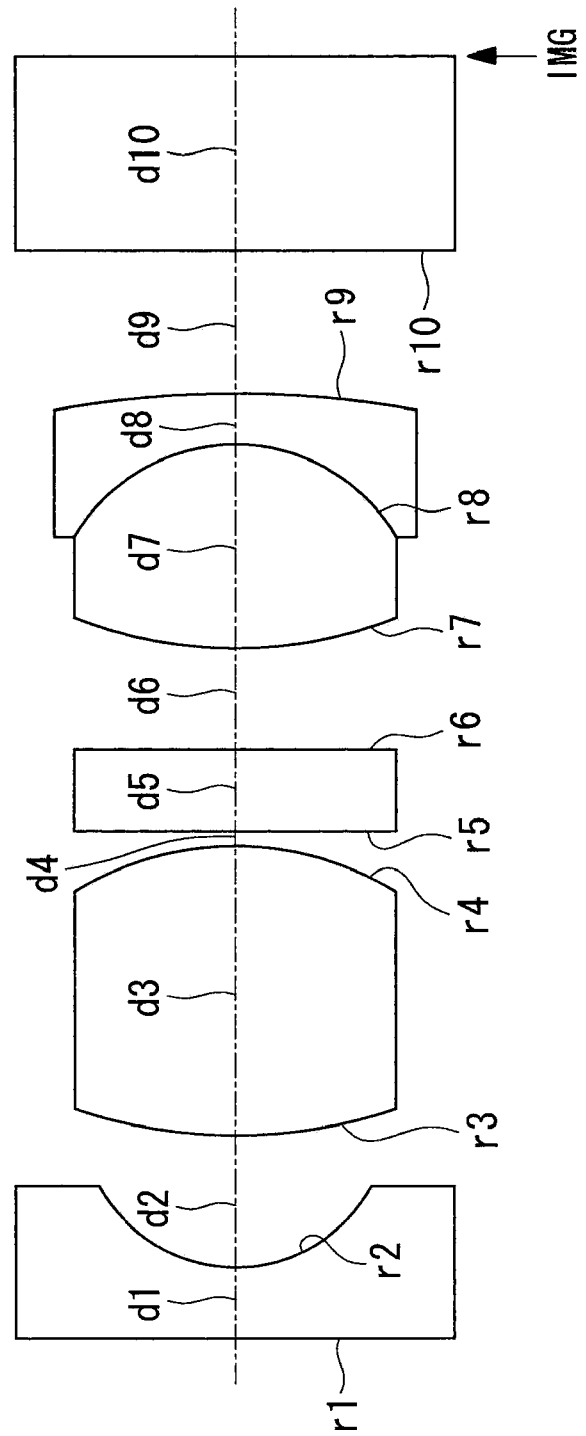
FIG. 20 is a lens cross-sectional diagram showing the overall structure of an objective optical system according to Example 8 of the present invention.
Figure 21:
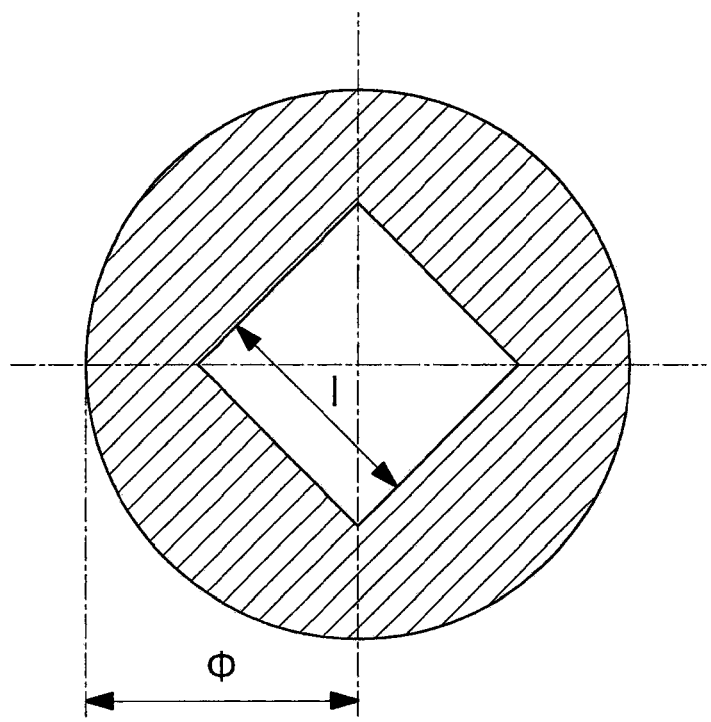
FIG. 21 is a front view of an aperture stop provided in the objective optical system of Example 8 of the present invention.

An objective optical system according to Example 8 of the present invention has a lens structure shown in FIG. 20 and the following lens data. The aperture stop in this Example is formed on the image-side surface of a cover glass (Surface No. 5). As shown in FIG. 21, the aperture stop includes an opening having a circular outer shape with a radius Φ=0.24 mm centered on the optical axis and a light-blocking portion with a square shape of side length l=0.198 mm centered on the optical axis. In conditional expression (1), Q=21.7.

| lens data | | | | |
|---|---|---|---|---|
| surface number | r | d | ne | vd |
| OBJ | ∞ | 17.00 | 1. | |
| 1 | ∞ | 0.36 | 1.88814 | 40.78 |
| 2 | 0.7364 | 0.64 | 1. | |
| 3 | 2.7059 | 1.42 | 1.73234 | 54.68 |
| 4 | −1.5183 | 0.10 | 1. | |
| 5(S) | ∞ | 0.38 | 1.52495 | 59.89 |
| 6 | ∞ | 0.51 | 1. | |
| 7 | 2.2462 | 0.99 | 1.69979 | 55.53 |
| 8 | −0.9387 | 0.25 | 1.85504 | 23.78 |
| 9 | −5.8320 | 0.72 | 1. | |
| 10 | ∞ | 0.95 | 1.51825 | 64.14 |
| IMG | ∞ | 0.00 | | |

| Miscellaneous Data | |
|---|---|
| Image height | 0.971 |
| Focal distance | 1.00001 |
| Total lens length | 6.3091 |
| F-number | 4.415 |
| Viewing angle | 135.4° |

Example 9

Figure 22:
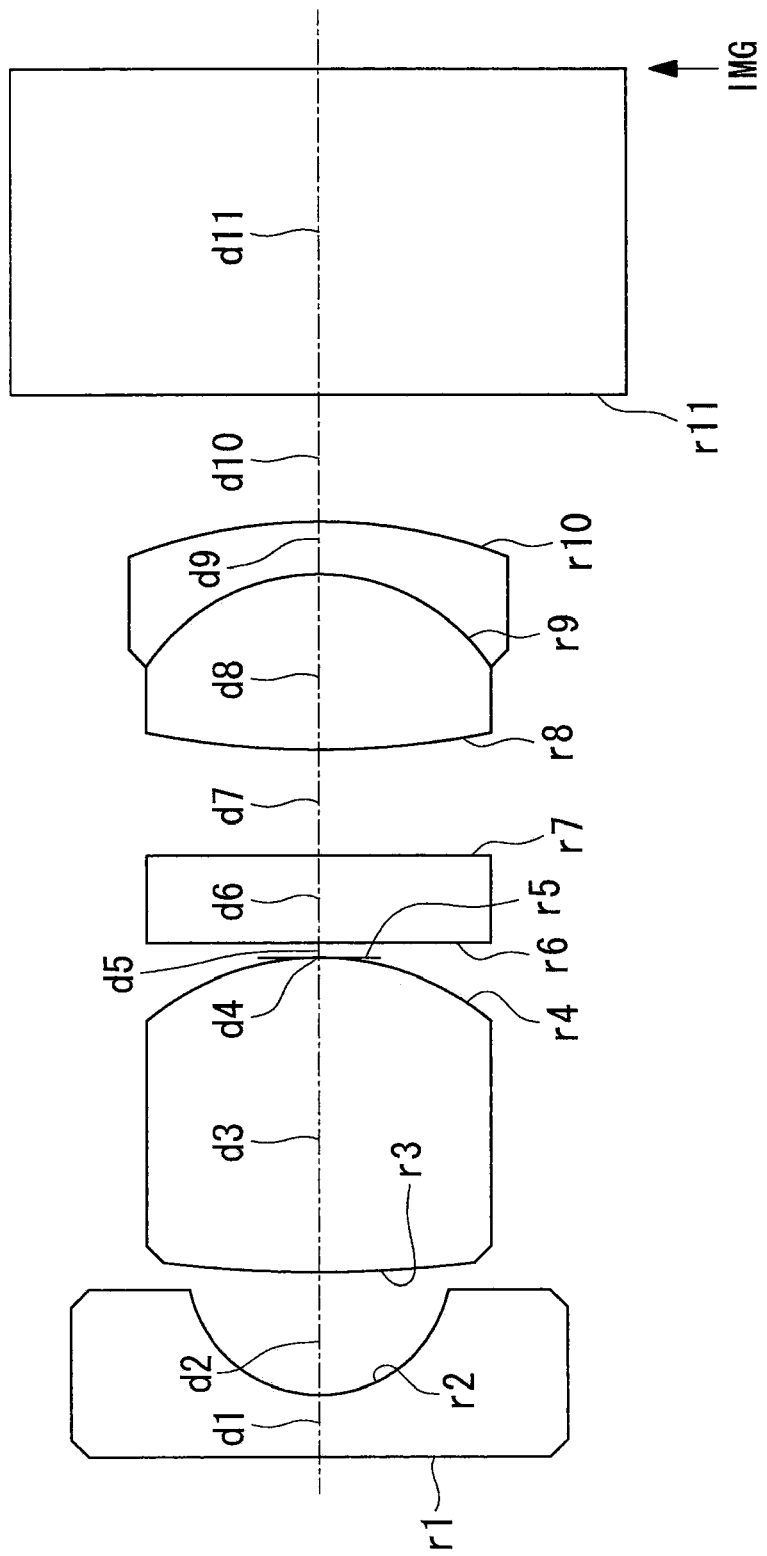
FIG. 22 is a lens cross-sectional diagram showing the overall structure of an objective optical system according to Example 9 of the present invention.
Figure 23:
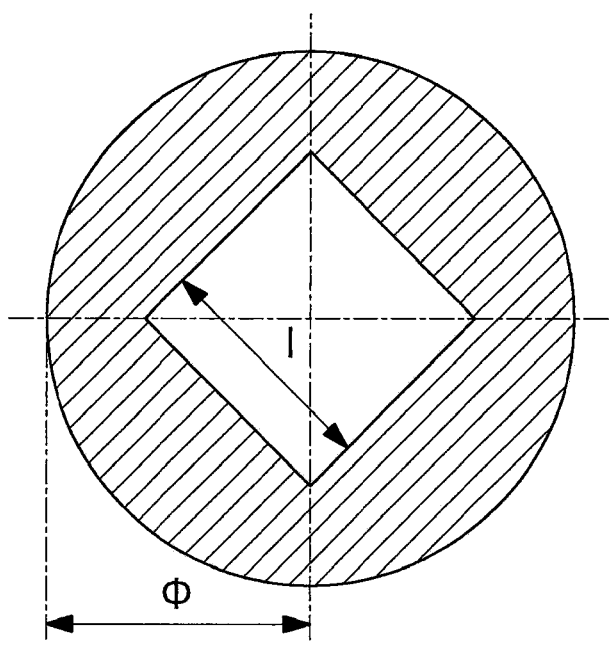
FIG. 23 is a front view of an aperture stop provided in the objective optical system of Example 9 of the present invention.

An objective optical system according to Example 9 of the present invention has a lens structure shown in FIG. 22 and the following lens data. The aperture stop in this Example is disposed between a second lens and a cover glass (Surface No. 5). As shown in FIG. 23, the aperture stop includes an opening having a circular outer shape with a radius Φ=0.26 mm and a light-blocking portion with a square shape of side length l=0.226 mm centered on the optical axis. In conditional expression (1), Q=24.1.

| lens data | | | | |
|---|---|---|---|---|
| surface number | r | d | ne | vd |
| OBJ | ∞ | 15.50 | 1. | |
| 1 | ∞ | 0.35 | 1.77066 | 71.79 |
| 2 | 0.7698 | 0.71 | 1. | |
| 3 | 14.2136 | 1.79 | 1.73234 | 54.68 |
| 4 | −1.5257 | 0.03 | 1. | |
| 5(S) | ∞ | 0.04 | 1. | |
| 6 | ∞ | 0.50 | 1.49557 | 75.00 |
| 7 | ∞ | 0.62 | 1. | |
| 8 | 5.3840 | 1.00 | 1.79196 | 47.37 |
| 9 | −1.2014 | 0.29 | 1.93430 | 18.90 |
| 10 | −3.2349 | 0.73 | 1. | |
| 11 | ∞ | 1.85 | 1.61379 | 50.20 |
| IMG | ∞ | 0.00 | | |

| Miscellaneous Data | |
|---|---|
| Image height | 1.02 |
| Focal distance | 1.00001 |
| Total lens length | 7.902 |
| F-number | 1.452 |
| Viewing angle | 149.6° |

Example 10

Figure 24:
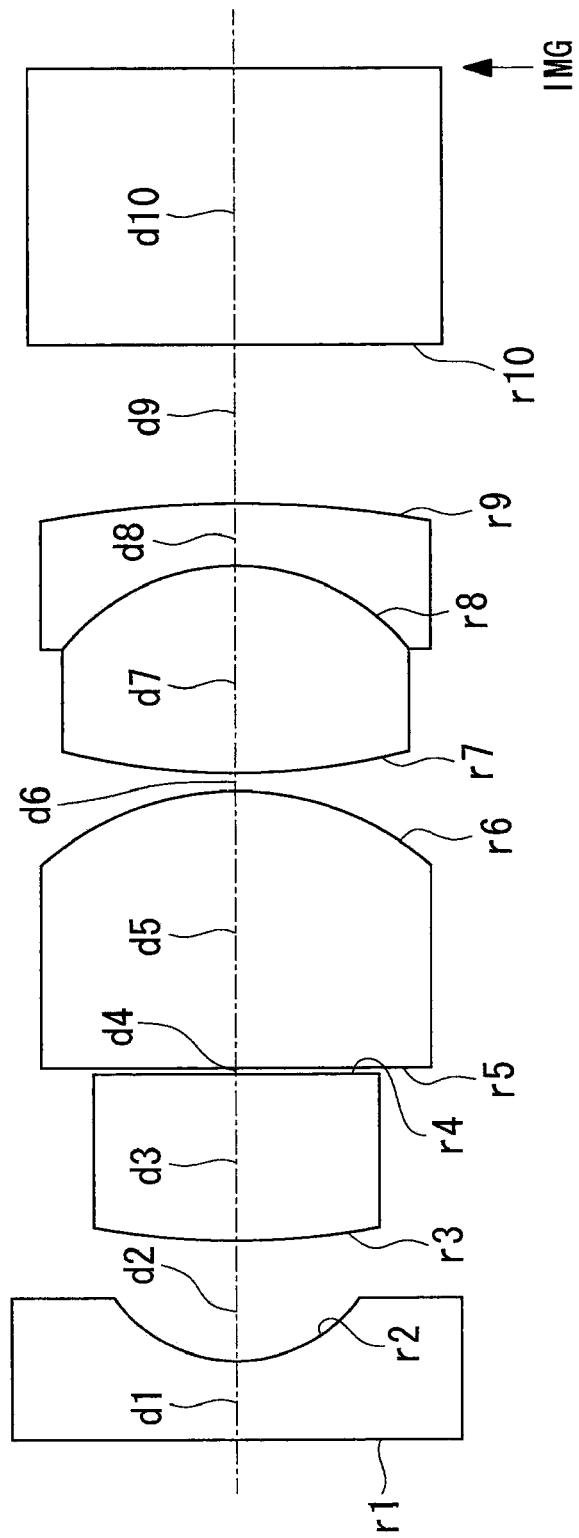
FIG. 24 is a lens cross-sectional diagram showing the overall structure of an objective optical system according to Example 10 of the present invention.
Figure 25:
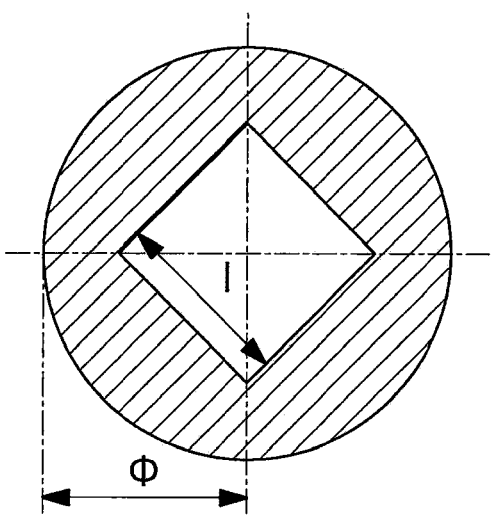
FIG. 25 is a front view of an aperture stop provided in the objective optical system of Example 10 of the present invention.

An objective optical system according to Example 10 of the present invention has a lens structure shown in FIG. 24 and the following lens data. The aperture stop in this Example is formed on the flat surface of a plano-convex lens (Surface No. 4). As shown in FIG. 25, the aperture stop includes an opening having a circular outer shape with a radius Φ=0.26 mm centered on the optical axis and a light-blocking portion with a square shape of side length l=0.24 mm centered on the optical axis. In conditional expression (1), Q=27.1.

| lens data | | | | |
|---|---|---|---|---|
| surface number | r | d | ne | vd |
| OBJ | ∞ | 13.60 | 1. | |
| 1 | 34.3018 | 0.45 | 1.88815 | 40.76 |
| 2 | 0.8496 | 0.69 | 1. | |
| 3 | 5.3201 | 0.93 | 1.83932 | 37.16 |
| 4(S) | ∞ | 0.03 | 1. | |
| 5 | ∞ | 1.58 | 1.81078 | 40.88 |
| 6 | −1.7164 | 0.11 | 1. | |
| 7 | 4.1479 | 1.18 | 1.73234 | 54.68 |
| 8 | −1.2969 | 0.35 | 1.93429 | 18.90 |
| 9 | −6.0600 | 0.89 | 1. | |
| 10 | ∞ | 1.56 | 1.51825 | 64.14 |
| IMG | ∞ | 0.00 | | |

| Miscellaneous data | |
|---|---|
| Image height | 1.00 |
| Focal distance | 1.00001 |
| Total lens length | 7.7648 |
| F-number | 4.078 |
| Viewing angle | 136.7° |

Example 11

Figure 26:
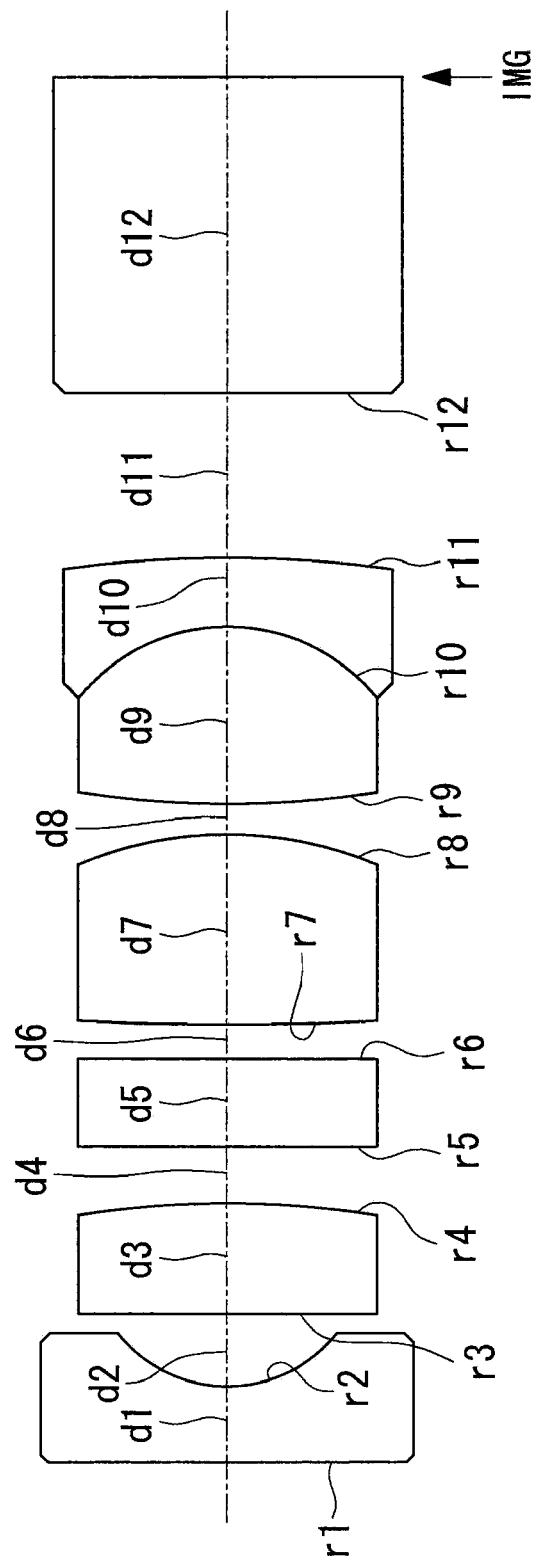
FIG. 26 is a lens cross-sectional diagram showing the overall structure of an objective optical system according to Example 11 of the present invention.
Figure 27:
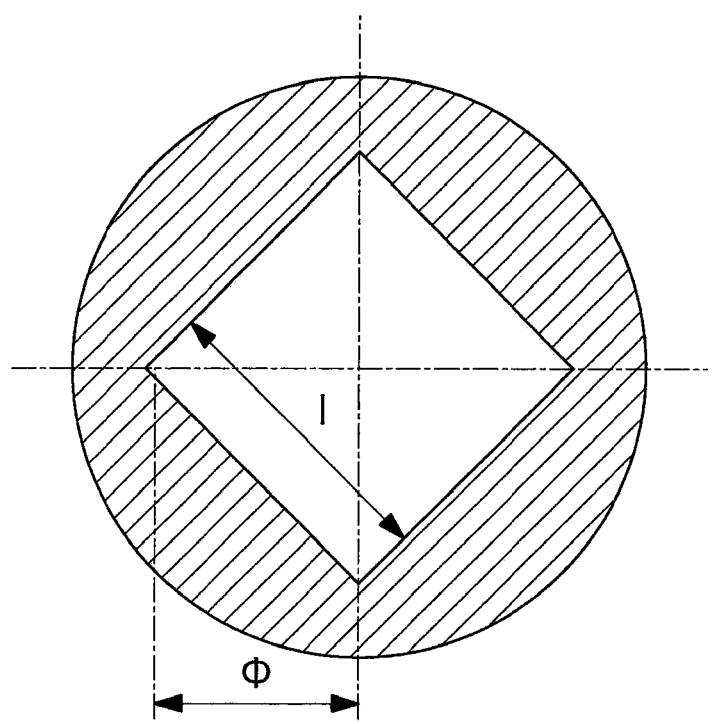
FIG. 27 is a front view of an aperture stop provided in the objective optical system of Example 11 of the present invention.

An objective optical system according to Example 11 of the present invention has a lens structure shown in FIG. 26 and the following lens data. The aperture stop in this Example is formed on the image-side surface of a cover glass (Surface No. 6). As shown in FIG. 27, the aperture stop includes an opening having a circular outer shape with a radius Φ=0.31 mm centered on the optical axis and a light-blocking portion with a square shape of side length l=0.325 mm centered on the optical axis. In conditional expression (1), Q=35.0.

| lens data | | | | |
|---|---|---|---|---|
| surface number | r | d | ne | vd |
| OBJ | ∞ | 14.50 | 1. | |
| 1 | ∞ | 0.50 | 2.18246 | 33.01 |
| 2 | 0.9456 | 0.46 | 1. | |
| 3 | ∞ | 0.72 | 1.93429 | 18.90 |
| 4 | −7.4010 | 0.40 | 1. | |
| 5 | ∞ | 0.56 | 1.51564 | 75.00 |
| 6(S) | ∞ | 0.23 | 1. | |
| 7 | 18.8830 | 1.24 | 2.18246 | 33.01 |
| 8 | −2.6600 | 0.20 | 1. | |
| 9 | 6.2845 | 1.17 | 1.73234 | 54.68 |
| 10 | −1.3129 | 0.45 | 1.93429 | 18.90 |
| 11 | −8.7654 | 1.10 | 1. | |
| 12 | ∞ | 2.06 | 1.51825 | 64.14 |
| IMG | ∞ | 0.00 | | |

| Miscellaneous Data | |
|---|---|
| Image height | 0.935 |
| Focal distance | 1.00002 |
| Total lens length | 9.089 |
| F-number | 4.119 |
| Viewing angle | 128.7° |

Example 12

Figure 28:
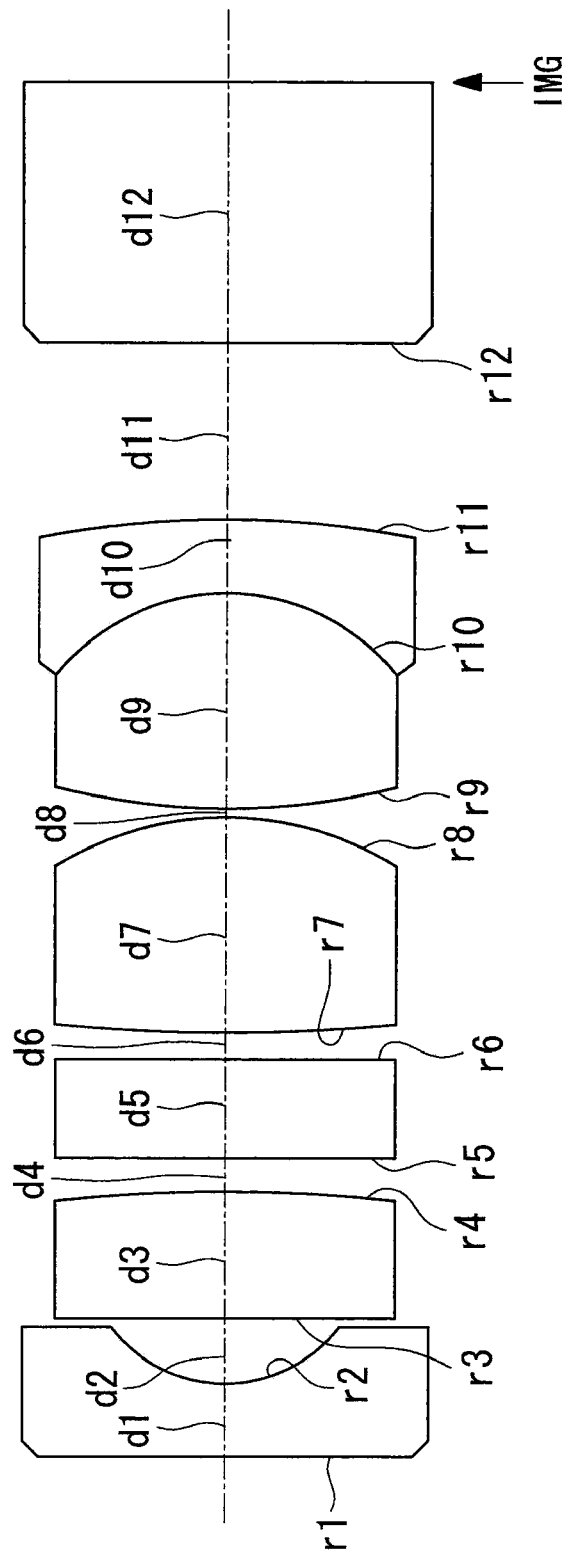
FIG. 28 is a lens cross-sectional diagram showing the overall structure of an objective optical system according to Example 12 of the present invention.
Figure 29:
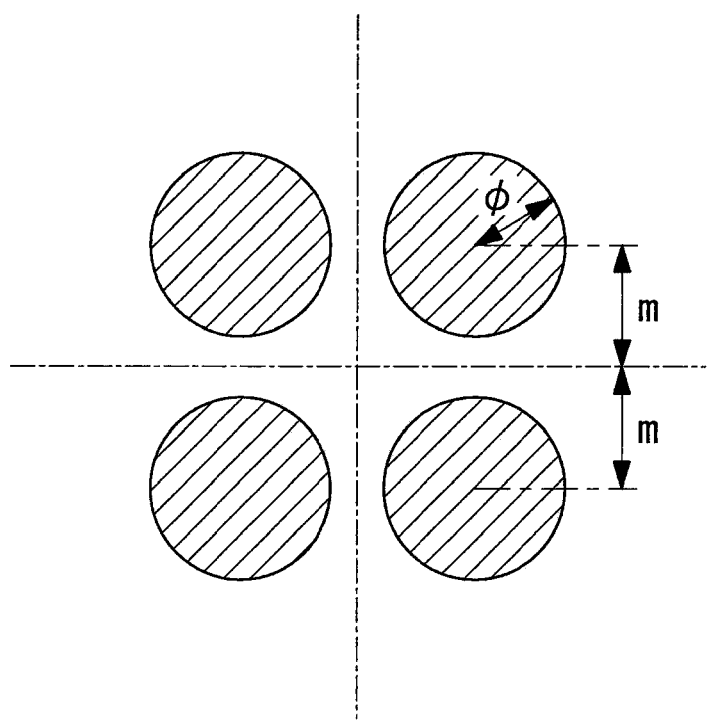
FIG. 29 is a front view of an aperture stop provided in the objective optical system of Example 12 of the present invention.

An objective optical system according to Example 12 of the present invention has a lens structure shown in FIG. 28 and the following lens data. The aperture stop in this Example is formed on the image-side surface of a cover glass (Surface No. 6). As shown in FIG. 29, the aperture stop includes four openings arranged in a square centered on the optical axis and a light-blocking portion that is the portion excluding these openings. The radius of the openings is φ=0.0926 mm, and half of the center-to-center distance between the openings is m=0.120 mm.

| lens data | | | | |
|---|---|---|---|---|
| surface number | r | d | ne | vd |
| OBJ | ∞ | 13.50 | 1. | |
| 1 | ∞ | 0.41 | 1.88815 | 40.76 |
| 2 | 0.8450 | 0.38 | 1. | |
| 3 | ∞ | 0.74 | 1.85504 | 23.78 |
| 4 | −9.6236 | 0.19 | 1. | |
| 5 | ∞ | 0.57 | 1.51564 | 75.00 |

-continued

| lens data | | | | |
|---|---|---|---|---|
| 6(S) | ∞ | 0.16 | 1. | |
| 7 | 9.4949 | 1.25 | 1.83932 | 37.16 |
| 8 | −1.9677 | 0.05 | 1. | |
| 9 | 3.9867 | 1.25 | 1.69979 | 55.53 |
| 10 | −1.2696 | 0.43 | 1.93429 | 18.90 |
| 11 | −5.8760 | 1.01 | 1. | |
| 12 | ∞ | 1.50 | 1.51825 | 64.14 |
| IMG | ∞ | 0.00 | | |

| Miscellaneous Data | |
|---|---|
| Image height | 0.96 |
| Focal distance | 1.00001 |
| Total lens length | 7.937 |
| F-number | 1.624 |
| Viewing angle | 131.2° |

Example 13

Figure 30:
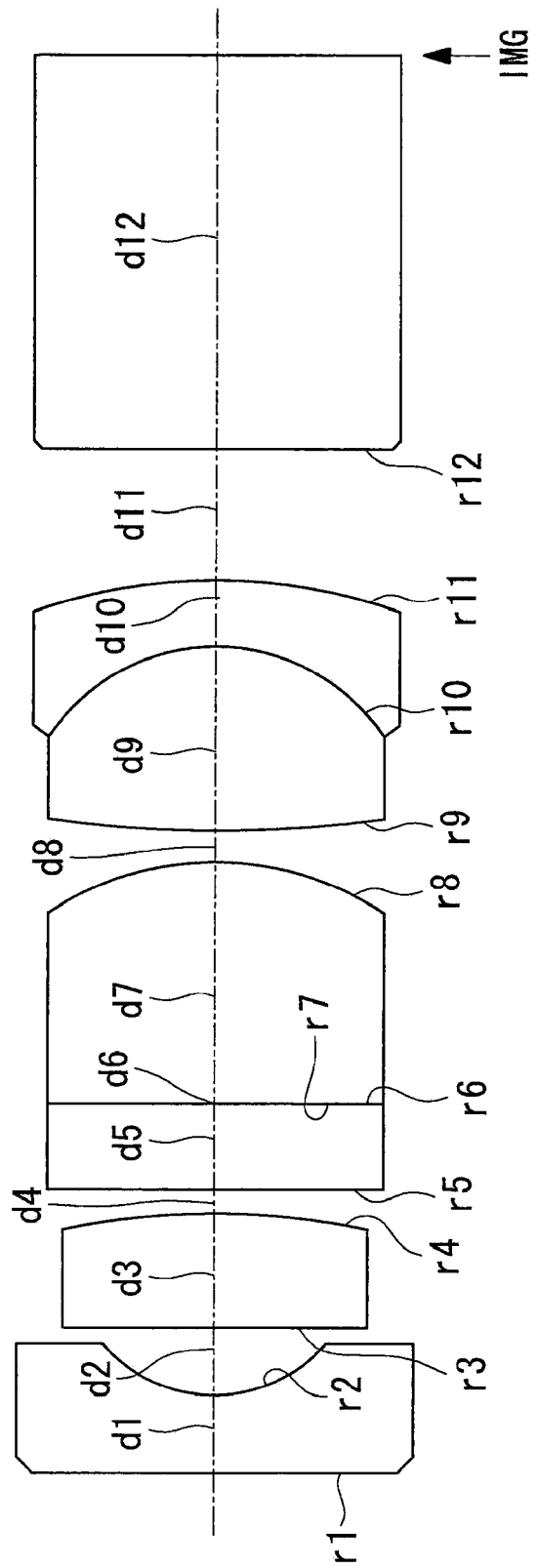
FIG. 30 is a lens cross-sectional diagram showing the overall structure of an objective optical system according to Example 13 of the present invention.
Figure 31:
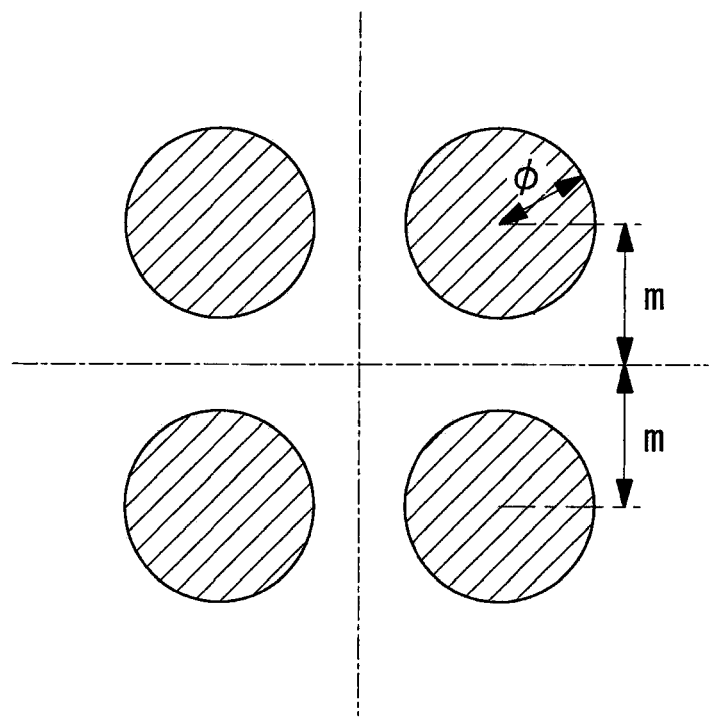
FIG. 31 is a front view of an aperture stop provided in the objective optical system of Example 13 of the present invention.

An objective optical system according to Example 13 of the present invention has a lens structure shown in FIG. 30 and the following lens data. The aperture stop in this Example is formed on the joining surface of a cover glass and a plano-convex lens (Surface No. 6). As shown in FIG. 31, the aperture stop includes four openings in a square arrangement centered on the optical axis and a light-blocking portion that is the portion excluding these openings. The radius of the openings is φ=0.093 mm, and half of the center-to-center distance between the openings is m=0.140 mm.

| lens data | | | | |
|---|---|---|---|---|
| surface number | r | d | ne | vd |
| OBJ | ∞ | 14.80 | 1. | |
| 1 | ∞ | 0.50 | 2.18246 | 33.01 |
| 2 | 0.9683 | 0.42 | 1. | |
| 3 | ∞ | 0.72 | 1.93429 | 18.90 |
| 4 | −5.4027 | 0.15 | 1. | |
| 5 | ∞ | 0.56 | 1.51564 | 75.00 |
| 6(S) | ∞ | 0.00 | 1. | |
| 7 | ∞ | 1.54 | 1.88815 | 40.76 |
| 8 | −2.0953 | 0.20 | 1. | |
| 9 | 6.8599 | 1.18 | 1.73234 | 54.68 |
| 10 | −1.3201 | 0.43 | 1.93429 | 18.90 |
| 11 | −3.7233 | 0.85 | 1. | |
| 12 | ∞ | 2.50 | 1.51825 | 64.14 |
| IMG | ∞ | 0.00 | | |

| Miscellaneous Data | |
|---|---|
| Image height | 0.94 |
| Focal distance | 0.99999 |
| Total lens length | 9.042 |
| F-number | 1.565 |
| Viewing angle | 127.1° |

Example 14

Figure 32:
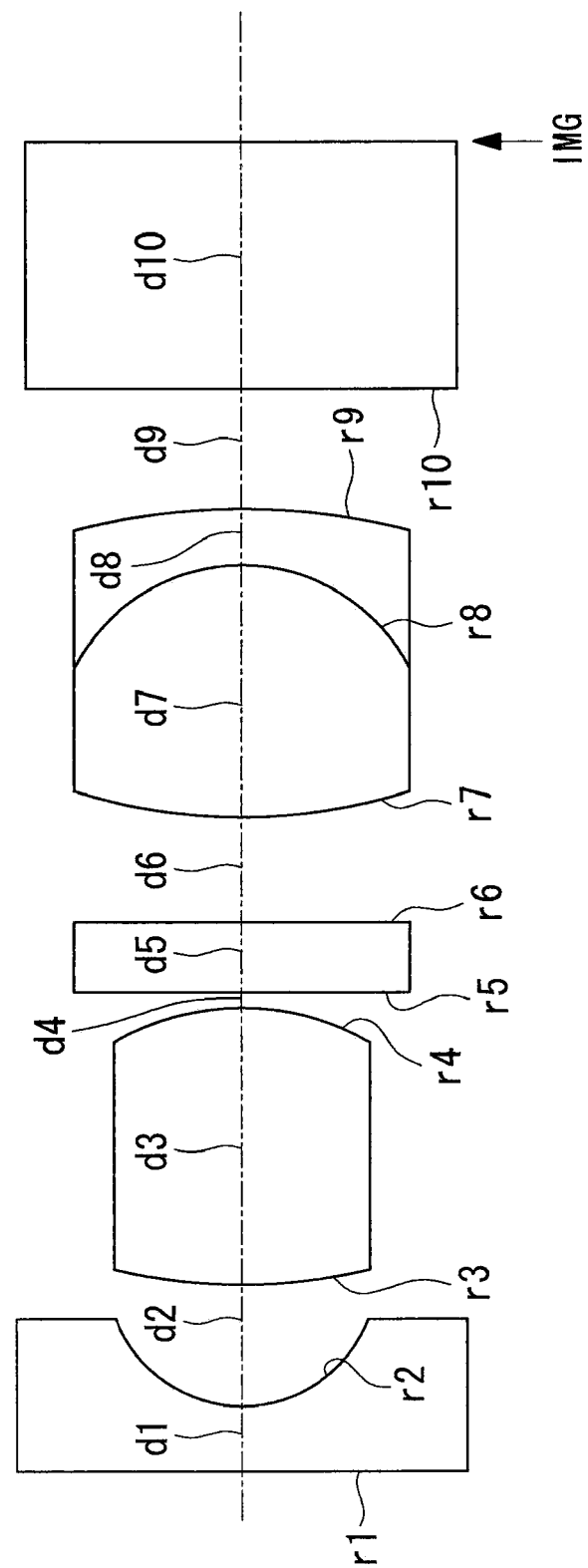
FIG. 32 is a lens cross-sectional diagram showing the overall structure of an objective optical system according to Example 14 of the present invention.
Figure 33:
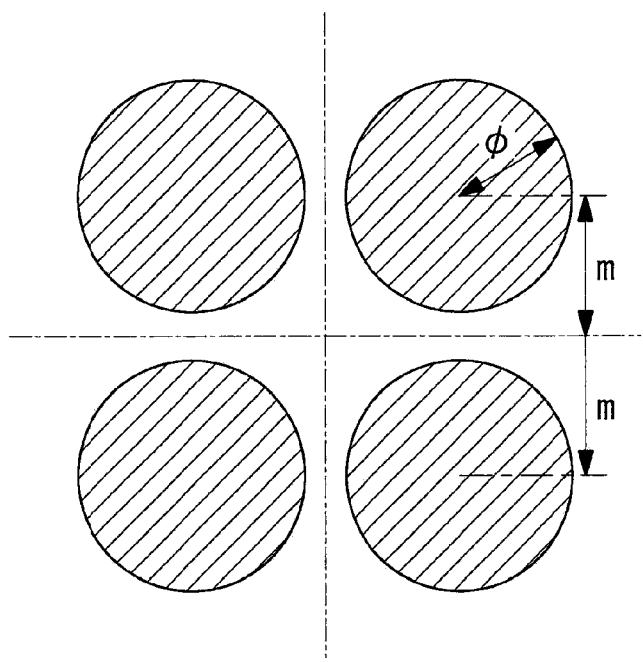
FIG. 33 is a front view of an aperture stop provided in the objective optical system of Example 14 of the present invention.

An objective optical system according to Example 14 of the present invention has a lens structure shown in FIG. 32 and the following lens data. The aperture stop in this Example is formed on the object-side surface of a cover glass (Surface No. 5). As shown in FIG. 33, the aperture stop includes four openings in a square arrangement centered on the optical axis and a light-blocking portion that is the portion excluding these openings. The radius of the openings is φ=0.120 mm, and half of the center-to-center distance between the openings is m=0.144 mm.

| lens data | | | | |
|---|---|---|---|---|
| surface number | r | d | ne | vd |
| OBJ | ∞ | 19.80 | 1. | |
| 1 | ∞ | 0.33 | 1.88814 | 40.78 |
| 2 | 0.6783 | 0.60 | 1. | |
| 3 | 3.5348 | 1.37 | 1.73234 | 54.68 |
| 4 | −1.3630 | 0.09 | 1. | |
| 5(S) | ∞ | 0.35 | 1.52495 | 59.89 |
| 6 | ∞ | 0.52 | 1. | |
| 7 | 2.9104 | 1.26 | 1.69979 | 55.53 |
| 8 | −0.9191 | 0.26 | 1.85504 | 23.78 |
| 9 | −3.8252 | 0.60 | 1. | |
| 10 | ∞ | 1.23 | 1.51825 | 64.14 |
| IMG | ∞ | 0.00 | | |

| Miscellaneous data | |
|---|---|
| Image height | 0.895 |
| Focal distance | 0.99988 |
| Lens overall length | 6.6 |
| F-number | 2.091 |
| Viewing angle | 117.1° |

The depth-of-field extending effect achieved by the objective optical systems according to Examples 1 to 14 of the present invention described above, as well as the imaging devices provided with these objective optical systems, will be described next.

As shown in Table 1, for the objective optical system according to each Example, the depth of field is calculated on the basis of the resolution of the imaging element assumed to be used. Specifically, the range in the optical axis direction where the MTF for a spatial frequency corresponding to 2.5 pixels of the imaging element is 10% or more is calculated as the depth of field.

TABLE 1

| | Pixel Pitch | Depth of field (present invention) | Depth of field (Comparative Example) |
|---|---|---|---|
| Example 1 | 1.5 | 9.0-100 | 12.5-100 |
| Example 2 | 1.6 | 7.8-100 | 11.6-100 |
| Example 3 | 1.5 | 7.7-100 | 10.8-100 |
| Example 4 | 1.6 | 6.4-100 | 9.6-100 |
| Example 5 | 1.7 | 5.8-100 | 9.0-100 |
| Example 6 | 1.4 | 10.5-100 | 12.1-100 |
| Example 7 | 1.6 | 9.7-100 | 12.2-100 |
| Example 8 | 1.6 | 9.0-100 | 11.6-100 |
| Example 9 | 1.5 | 8.1-100 | 12.0-100 |
| Example 10 | 1.6 | 6.9-100 | 12.6-100 |
| Example 11 | 1.5 | 7.5-100 | 12.8-100 |
| Example 12 | 1.5 | 7.0-100 | 10.7-100 |
| Example 13 | 1.4 | 7.8-100 | 12.1-100 |
| Example 14 | 1.6 | 9.5-100 | 12.2-100 |

For example, in the case of Example 1, the objective optical system is used in combination with an imaging element whose pitch, which is the center-to-center distance between adjacent pixels in the direction in which they are arranged, is 1.5 μm. The spatial frequency f corresponding to 2.5 pixels in this case is calculated as spatial frequency $f = 1/(2.5 \times 1.5e^{-3}) = 266.7$ (lines/mm)

Figure 34:
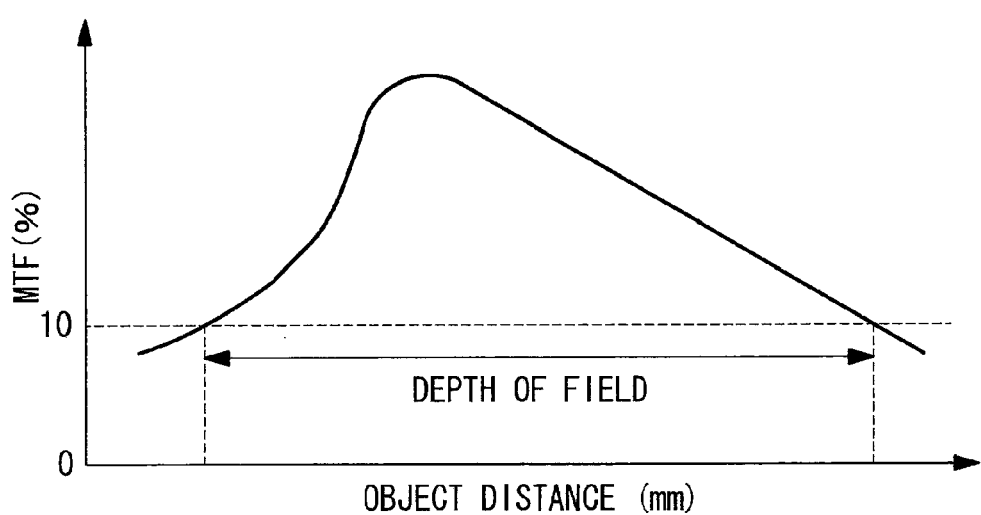
FIG. 34 is a graph schematically showing the relationship between the MTF at a prescribed spatial frequency and the object distance.

Next, at each position in the optical axis direction of the field of view of the objective optical system, when the MTF corresponding to a spatial frequency of 266.7 (lines/mm) is calculated, an MTF graph as shown in FIG. 34 is obtained. As shown in FIG. 34, the MTF changes according to the distance from the distal end face of the objective optical system (the object distance); the MTF takes a maximum at an object distance corresponding to the focal position of the objective optical system and decreases as the object distance becomes closer or farther than the focal position. In such a graph, the region of object positions where the MTF becomes 10% or higher is calculated as the depth of field.

Also, as Comparative Examples, the depths of field (unit: mm) of objective optical systems having lens structures identical to those of the objective optical systems according to each of the Examples of the present invention and in which only the aperture stops are replaced with conventional aperture stops are calculated by the same method. Specifically, in the Comparative Examples for Example 1 to Example 14, the depths of field of objective optical systems provided with aperture stops having only one opening of radius Φ or φ are calculated.

The depths of field of the objective optical systems according to Examples 1 to 14 of the present invention and the objective optical systems according to each of the Comparative Examples are as shown in Table 1. Thus, the objective optical systems according to Examples 1 to 14 of the present invention have depths of field that are all wider compared with those of the objective optical systems provided with the conventional aperture stops.

REFERENCE SIGNS LIST

1 objective optical system
2 imaging element
10 imaging device
L1 to L5 lenses
F1, F2 parallel flat plate
A opening
B light-blocking portion
C peripheral portion
O optical axis
S, S' aperture stops

The invention claimed is:
1. An imaging device comprising:
an objective optical system that comprises an aperture stop that is disposed at an intermediate position on an optical axis; and
an imaging element that includes pixels arranged in a square along two mutually orthogonal axial directions and that acquires an optical image of an object, which is formed by the objective optical system, wherein
the objective optical system comprises a plurality of lenses, all of the lenses have a shape that is rotationally symmetric with respect to the optical axis, the aperture stop includes
a single opening that allows incident light from the object to pass there through and a single light-blocking portion that blocks the incident light,
the opening and the light-blocking portion being formed on a same plane intersecting the optical axis,
the light-blocking portion is a square-shaped region that is formed at a portion aligned with the optical axis and that has sides inclined at 45° relative to the directions in which the pixels are arranged, and
the opening is an annular-shaped region that is formed around the light-blocking portion.
2. The imaging device according to claim 1, wherein the aperture stop satisfies conditional expression (a) below:

$$4 < Q < 50, \quad \text{(a)}$$

where Q is (an area of the light-blocking portion (mm$^2$)/an area of the opening (mm$^2$))×100.
3. The imaging device according to claim 1, wherein the light-blocking portion is formed by forming a metal film on a glass surface.
4. An endoscope comprising an imaging device according to claim 1.
5. The imaging device according to claim 1, wherein the opening has a circular outer shape.
6. The imaging device according to claim 1, wherein both the opening and the light-blocking portion are centered on the optical axis.

* * * * *